(12) United States Patent
Mita et al.

(10) Patent No.: US 6,420,398 B2
(45) Date of Patent: Jul. 16, 2002

(54) UREA DERIVATIVES HAVING NITROGEN AROMATIC HETEROCYCLE

(75) Inventors: Shiro Mita; Masato Horiuchi; Masakazu Ban; Hiroshi Suhara, all of Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/775,420

(22) Filed: Feb. 1, 2001

Related U.S. Application Data

(63) Continuation of application No. PCT/JP99/04242, filed on Aug. 4, 1999.

(30) Foreign Application Priority Data

Aug. 5, 1998 (JP) ............................................. 10-221506

(51) Int. Cl.[7] ........................ C07D 213/02; A61K 31/44
(52) U.S. Cl. ...................... 514/357; 514/588; 546/336; 564/63
(58) Field of Search .................... 546/336; 514/357, 514/588; 564/63

(56) References Cited

U.S. PATENT DOCUMENTS

| 5,190,974 A | 3/1993 | Clemence et al. ........... 514/513 |
| 5,674,864 A | 10/1997 | Clemence et al. ........... 514/212 |

FOREIGN PATENT DOCUMENTS

| JP | 63-246739 A | 10/1988 |
| JP | 4 230358 A | 8/1992 |
| JP | 9-508115 A | 8/1997 |
| WO | WO 95/19957 | 7/1995 |

OTHER PUBLICATIONS

Davidovich, Yu. A. et al, "Synthesis of bis (isocyanatoethyl) disulfide and its conversion of ureas", Izv. Akad. Nauk SSSR, Ser. Khim., No. 8, pp. 1918–1920 (1989).

Yamazaki, Clinical Immunology, 27, pp. 1270–1274 (and an English language Abstract thereof) (1995).

A. Eigler et al, "Taming TNF: strategies to restrain this proinflammatory cytokine", Immunology Today, vol. 18, No. 10, pp. 487–492 (Oct. 1997).

*Primary Examiner*—Zinna Northington Davis
(74) *Attorney, Agent, or Firm*—Frishauf, Holtz, Goodman & Chick, P.C.

(57) ABSTRACT

An object of the present invention is to provide novel urea derivatives which have TNF-α production inhibitory effects and are useful as therapeutic agents for various diseases, particularly as therapeutic agents for autoimmune diseases such as rheumatoid arthritis. The urea derivatives according to the present invention are compounds represented by the formula [I] and salts thereof. In the formula, $R^1$ is H, alkyl, phenyl or a group of the formula ['I]; $R^2$ is H, alkyl, carboxyl or ester thereof or the like; $R^3$ and $R^4$ are each H, alkyl, cycloalkyl or the like; $R^5$ is H, alkyl, hydroxy or the like; $R^6$ is a nitrogen aromatic heterocycle; and $A^1$ and $A^2$ are alkylene.

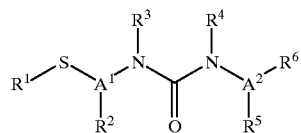

[I]

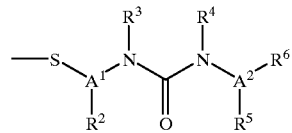

[II]

23 Claims, No Drawings

UREA DERIVATIVES HAVING NITROGEN AROMATIC HETEROCYCLE

This application is a continuation application of International application PCT/JP99/04242 filed Aug. 4, 1999.

TECHNICAL FIELD

The present invention relates to novel urea derivatives which have TNF-α production inhibitory effects and are useful as therapeutic agents for various diseases, particularly as therapeutic agents for autoimmune diseases such as rheumatoid arthritis.

BACKGROUND ART

TNF-α (tumor necrosis factor-α) was found as a factor which induces hemorrhagic necrosis at tumor sites, and it is now recognized as a cytokine which widely participates in biophylaxis-immune mechanism through inflammation. However, prolonged and excessive production of TNF-α causes tissue disorders and is a factor which brings about causes and exacerbation of various diseases. Accordingly, it is reported that it is important to suppress the excessive production of TNF-α in morbidity where TNF-α is excessively produced (Yamazaki, Clinical Immunology, 27, 1270, 1995). The above-mentioned literature recites many pathema such as arthrorheumatism, systemic lupus erythematosus (SLE), cachexia, acute infectious disease, allergy, pyrexia, anemia and diabetes as examples of pathema in which TNF-α participates.

It is reported that TNF-α plays an important role in crises of rheumatoid arthritis and Crohn's disease, which are autoimmune diseases (Andreas Eigler et al., Immunology Today, 18, 487, 1997).

TNF-α is known to participate in various diseases as well as autoimmune diseases such as rheumatoid arthritis, Crohn's disease and systemic lupus erythematosus as reported in the above-mentioned literatures and the like. Compounds which inhibit its production or suppress its effect are expected to be useful for treatment of various diseases, and many studies have been done. Outlines of these studies of drugs are introduced in the above-mentioned literatures (Yamazaki, Clinical Immunology, 27, 1270, 1995, Andreas Eigler et al., Immunology Today, 18, 487, 1997). Recently, it was found that a proteolytic enzyme participating in secretion of TNF-α is metalloprotease, and a study of TNF-α production inhibitory effects of metalloprotease inhibitors is also reported (Published Japanese Translation of PCT No. 508115/1997).

Various drugs having the TNF-α production inhibitory effects have been studied as mentioned above. Focusing attention on chemical structure of the drugs, however, no drug having a chemical structural feature of compounds of the present invention is known at all. The chemical structural feature of the compounds of the present invention is that the compounds have urea structure as basic structure and have a sulfur atom and a nitrogen aromatic heterocycle in side chains. Few studies of such drugs having the urea structure as basic skeleton have been reported. Moreover, no drug having a sulfur atom in a side chain has hitherto practically been reported.

Since the compounds having the urea structure as the basic structure and having a sulfur atom and the nitrogen aromatic heterocycle in the side chains have not practically been reported as mentioned above, a study of synthesis of such compounds and a study of pharmacological actions, particularly the TNF-α production inhibitory effects of the compounds were very interesting subjects.

DISCLOSURE OF THE INVENTION

The present inventors focused attention on urea structure of which application to drugs had hardly been studied, made studies on synthesis of novel urea derivatives wherein sulfur is introduced into one side chain thereof and a nitrogen aromatic heterocycle is introduced into the other side chain thereof, and succeeded in preparing many novel compounds. The present inventors further studied pharmacological actions of the compounds and found that these novel compounds have excellent TNF-α production inhibitory effects.

The present invention relates to compounds represented by the following general formula [I] or salts thereof (hereinafter referred to as "the present compound" as far as there is no proviso), and pharmaceutical compositions containing it as an active ingredient.

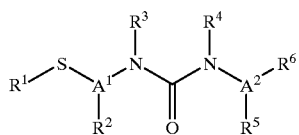

[wherein
$R^1$ is hydrogen, lower alkyl, phenyl or a group of the following formula [II].

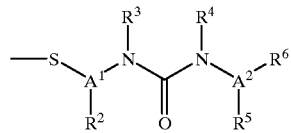

$R^2$ is hydrogen, lower alkyl, cycloalkyl, phenyl, carboxyl or ester thereof, and can join with sulfur adjacent to $A^1$ to form a nonaromatic heterocycle having sulfur in the ring.

$R^3$ and $R^4$, being the same or different, are hydrogen, lower alkyl, lower alkenyl, cycloalkyl, cycloalkenyl or phenyl.

$R^5$ is hydrogen, lower alkyl, hydroxy or lower alkoxy.

$R^6$ is an aromatic heterocycle having nitrogen in the ring.

$A^1$ and $A^2$, being the same or different, are lower alkylene.

Each lower alkyl defined above can be substituted by cycloalkyl, cycloalkenyl, adamantyl, phenyl, halogen, hydroxy, lower alkoxy, or an aromatic or nonaromatic heterocycle having nitrogen in the ring.

Each phenyl defined above can be substituted by lower alkyl, phenyl, hydroxy, lower alkoxy, halogeno-lower alkoxy, halogen, nitro, carboxyl or ester thereof.

The aromatic or nonaromatic heterocycle having nitrogen in the ring defined above can be substituted by lower alkyl, halogeno-lower alkyl, hydroxy-lower alkyl, cycloalkyl, phenyl, halogen, hydroxy or lower alkoxy.]

The groups defined above are hereinafter described in detail.

The lower alkyl is straight-chain or branched alkyl having one to eight carbon atoms such as methyl, ethyl, propyl, butyl, hexyl, isopropyl, isobutyl, isopentyl, isohexyl, t-butyl or 3,3-dimethylbutyl.

The lower alkenyl is straight-chain or branched alkenyl having two to eight carbon atoms such as vinyl, allyl, 3-butenyl, 5-hexenyl or isopropenyl.

The cycloalkyl is cycloalkyl having three to eight carbon atoms such as cyclopropyl, cyclobutyl, cyclopentyl, cyclohexyl or cycloheptyl.

The cycloalkenyl is cycloalkenyl having three to eight carbon atoms such as cyclopropenyl, cyclobutenyl, cyclopentenyl, cyclohexenyl or cycloheptenyl.

The lower alkoxy is straight-chain or branched alkoxy having one to eight carbon atoms such as methoxy, ethoxy, propoxy, butoxy, hexyloxy, isopropoxy or t-butoxy.

The halogen is fluorine, chlorine, bromine or iodine.

The lower alkylene is straight-chain or branched alkylene having one to eight carbon atoms such as methylene, ethylene, propylene, tetramethylene, pentamethylene, hexamethylene, methylmethylene, ethylethylene, dimethylethylene, propylethylene, isopropylethylene or methylpropylene.

The aromatic heterocycle having nitrogen in the ring is a monocyclic or condensed polycyclic aromatic heterocycle having one or two nitrogen atoms in the ring such as pyridine, pyrimidine, pyrrole, imidazole, oxazole, thiazole, quinoline, indole, benzimidazole, benzoxazole or benzothiazole.

The nonaromatic heterocycle having nitrogen in the ring is a nonaromatic heterocycle having one or two nitrogen atoms in the ring such as pyrrolidine, piperidine, morpholine, thiomorpholine, piperazine or homopiperazine.

The nonaromatic heterocycle having sulfur in the ring is a nonaromatic heterocycle having one or two sulfur atoms in the ring such as tetrahydrothiophene, thiolactone or dithiolane.

The ester is alkyl ester having one to eight carbon atoms such as methyl, ethyl or propyl, benzyl ester or phenyl ester.

In the present compounds, thiol, hydroxy and nitrogen of the nonaromatic heterocycle or the aromatic heterocycle can be protected with a protecting group.

The protecting group of thiol is a usual protecting group of thiol such as acyl or substituted thio.

In detail, examples of the protecting group are acyl such as lower alkanoyl, phenylcarbonyl, thenoyl or nicotinoyl; ester such as lower alkoxycarbonyl or substituted lower alkoxycarbonyl; substituted thio such as lower alkylthio or phenylthio; and substituted carbamoyl. Each phenyl ring of the phenylcarbonyl and the phenylthio can be substituted by halogen, lower alkyl, lower alkoxy or nitro.

Specific examples of preferred protecting groups of thiol are acyl such as acetyl, propionyl, butyryl, pivaloyl, benzoyl or thenoyl; ester such as t-butoxycarbonyl or benzyloxycarbonyl; and substituted thio such as ethylthio, t-butylthio or phenylthio.

The protecting group of hydroxy is a usual protecting group of hydroxy such as acyl, substituted lower alkyl or substituted silyl. In detail, examples of the protecting group are acyl such as formyl, lower alkanoyl, halogeno-lower alkanoyl or phenylcarbonyl; ester such as lower alkoxycarbonyl or phenyl-lower alkoxycarbonyl; substituted lower alkyl such as allyl, lower alkoxy-lower alkyl, substituted lower alkoxy-lower alkyl, phenyl-lower alkyl, tetrahydropyranyl or tetrahydrofuranyl; and substituted silyl such as lower alkylsilyl or phenylsilyl. Each phenyl ring of the phenylcarbonyl, the phenyl-lower alkoxycarbonyl, the phenyl-lower alkyl and the phenylsilyl can be substituted by halogen, lower alkyl, lower alkoxy or nitro.

Specific examples of preferred protecting groups of hydroxy are acyl such as formyl, acetyl, pivaloyl, monochloroacetyl, trichloroacetyl, trifluoroacetyl or benzoyl; ester such as methoxycarbonyl, ethoxycarbonyl, isobutoxycarbonyl, t-butoxycarbonyl or benzyloxycarbonyl; substituted alkyl such as allyl, methoxymethyl, 1-ethoxyethyl, 2-methoxyethoxymethyl, benzyloxymethyl, benzyl, 4-methoxybenzyl, trityl, 2-tetrahydropyranyl or 2-tetrahydrofuranyl; and substituted silyl such as trimethylsilyl, triethylsilyl, triisopropylsilyl, t-butyldimethylsilyl or t-butyldiphenylsilyl.

The protecting group of nitrogen of the nonaromatic heterocycle or the aromatic heterocycle is a usual protecting group of amino such as acyl, substituted lower alkyl or substituted sulfonyl.

In detail, examples of the protecting group are acyl such as formyl, lower alkanoyl, halogeno-lower alkanoyl or phenylcarbonyl; ester such as lower alkoxycarbonyl, substituted lower alkoxycarbonyl or phenoxycarbonyl; substituted lower alkyl such as allyl, phenyl-lower alkyl or benzoyl-lower alkyl; and substituted sulfonyl such as lower alkylsulfonyl or phenylsulfonyl. Each phenyl ring of the phenylcarbonyl, the phenoxycarbonyl, the phenyl-lower alkyl, the benzoyl-lower alkyl and the phenylsulfonyl can be substituted by halogen, lower alkyl, lower alkoxy or nitro.

Specific examples of preferred protecting groups of nitrogen of the nonaromatic heterocycle or the aromatic heterocycle are acyl such as formyl, acetyl, trichloroacetyl, trifluoroacetyl or benzoyl; ester such as methoxycarbonyl, isobutoxycarbonyl, t-butoxycarbonyl, allyloxycarbonyl, 2,2,2-trichloroethoxycarbonyl, benzyloxycarbonyl, diphenylmethoxycarbonyl or phenoxycarbonyl; substituted alkyl such as allyl, benzyl, trityl or (4-methoxyphenyl)diphenylmethyl; and substituted sulfonyl such as benzenesulfonyl, 2,4,6-trimethylbenzenesulfonyl or toluene-sulfonyl.

Salts in the present invention refer to any pharmaceutically acceptable salts, and examples thereof are salts with an inorganic acid such as hydrochloric acid, nitric acid or sulfuric acid, salts with an organic acid such as acetic acid, fumaric acid, maleic acid or tartaric acid, salts with an alkali metal or an alkaline-earth metal such as sodium, potassium or calcium, and the like. When geometrical isomers or optical isomers are present in the present compounds, these isomers are also included in the scope of the present invention. The present compounds can be in the form of hydrates.

Preferred examples of the present compound are compounds wherein the group(s) is (are) the followings in the compounds represented by the general formula [I] or salts thereof;

(1a) $R^1$ is a group selected from hydrogen, lower alkyl and the group of the general formula [II], wherein the lower alkyl can be substituted by phenyl; and/or (2a) $R^2$ is a group selected from hydrogen, lower alkyl, carboxyl and ester thereof; and/or
(3a) $R^2$ is a group joining with sulfur adjacent to $A^1$ to form a nonaromatic heterocycle selected from a tetrahydrothiophene ring and a thiolactone ring; and/or
(4a) $R^3$ and $R^4$, being the same or different, are groups selected from hydrogen and lower alkyl, wherein the lower alkyl can be substituted by a group selected from cycloalkyl, cycloalkenyl, adamantyl, phenyl, a pyridine ring and a piperidine ring, and further the phenyl can be substituted by a group selected from halogeno-lower alkoxy, halogen, carboxyl and ester thereof; and/or
(5a) $R^5$ is a group selected from hydrogen and lower alkyl; and/or
(6a) $R^6$ is an aromatic heterocycle having nitrogen in the ring selected from a pyridine ring, a pyrimidine ring, a pyrrole ring, an imidazole ring, a thiazole ring, an indole ring, a benzimidazole ring and a benzothiazole ring, wherein the aromatic heterocycle can be substituted by lower alkyl.

Namely,

Compounds defined by above (1a) in the compounds represented by the general formula [I] or salts thereof, Compounds defined by above (2a) in the compounds represented by the general formula [I] or salts thereof, Compounds defined by above (3a) in the compounds represented by the general formula [I] or salts thereof, Compounds defined by above (4a) in the compounds represented by the general formula [I] or salts thereof, Compounds defined by above (5a) in the compounds represented by the general formula [I] or salts thereof, Compounds defined by above (6a) in the compounds represented by the general formula [I] or salts thereof, and Compounds defined by any combination s of two or more of above (1a), (2a), (3a), (4a), (5a) and (6a) in the compounds represented by the general formula [I] or salts thereof.

More preferred examples of the present compound are compounds wherein the group(s) is (are) the followings in the compounds represented by the general formula [I] or salts thereof;
(1b) $R^1$ is a group selected from hydrogen and lower alkyl; and/or
(2b) $R^2$ is hydrogen; and/or
(3b) $R^3$ is lower alkyl, wherein the lower alkyl can be substituted by a group selected from cycloalkyl, cycloalkenyl, adamantyl and phenyl, and further the phenyl can be substituted by halogen; and/or
(4b) $R^4$ is hydrogen; and/or
(5 b) $R^5$ is hydrogen; and/or
(6b) $R^6$ is a pyridine ring.

Namely,

Compounds defined by above (1b) in the compounds represented by the general formula [I] or salts thereof, Compounds defined by above (2b) in the compounds represented by the general formula [I] or salts thereof, Compounds defined by above (3b) in the compounds represented by the general formula [I] or salts thereof, Compounds defined by above (4b) in the compounds represented by the general formula [I] or salts thereof, Compounds defined by above (5b) in the compounds represented by the general formula [I] or salts thereof, Compounds defined by above (6b) in the compounds represented by the general formula [I] or salts thereof, and Compounds defined by any combinations of two or more of above (1b), (2b), (3b), (4b), (5b) and (6b) in the compounds represented by the general formula [I] or salts thereof.

Further preferred examples of the present compound are compounds wherein the group(s) is (are) the followings in the compounds represented by the general formula [I] or salts thereof;
(1c) $R^1$ is a group selected from hydrogen, methyl, benzyl and the group of the general formula [II]; and/or
(2c) $R^2$ is a group selected from hydrogen, isopropyl and methoxycarbonyl; and/or
(3c) $R^2$ is a group joining with sulfur adjacent to $A^1$ to form a 2-oxotetrahydrothiophene ring or a tetrahydrothiophene ring; and/or
(4c) $R^3$ is a group selected from hydrogen, isopentyl, 2-cyclopentylethyl, 2-cyclohexylethyl, 2-cycloheptylethyl, 2-cyclooctylethyl, 2-(cyclohexen-1-yl)ethyl, 1-adamantylmethyl, 2-(1-adamantyl)ethyl, phenethyl, 2,2-diphenylethyl, 3-phenylpropyl, 4-fluorophenethyl, 4-(ethoxycarbonyl)phenethyl, 4-(trifluoromethoxy)phenethyl, 2-(1-piperidyl)ethyl and 2-(4-pyridyl)ethyl; and/or
(5c) $R^4$ is a group selected from hydrogen, 2-cyclohexylethyl and phenethyl; and/or
(6c) $R^5$ is hydrogen or methyl; and/or
(7c) $R^6$ is a group selected from 1-pyrrolyl, 1-imidazolyl, 4-(1-methylimidazolyl), 4-(2-methylthiazolyl), 2-pyridyl, 3-pyridyl, 4-pyridyl, 4-(1-methylpyridinium), 4-pyrimidinyl, 3-indolyl, 2 -benzimidazolyl and 2-benzothiazolyl; and/or
(8c) $A^1$ is ethylene or isopropylethylene; and/or
(9c) $A^2$ is a group selected from methylene, ethylene, methylmethylene, propylene, tetramethylene and pentamethylene.

Namely,

Compounds defined by above (1c) in the compounds represented by the general formula [I] or salts thereof, Compounds defined by above (2c) in the compounds represented by the general formula [I] or salts thereof, Compounds defined by above (3c) in the compounds represented by the general formula [I] or salts thereof, Compounds defined by above (4c) in the compounds represented by the general formula [I] or salts thereof, Compounds defined by above (5c) in the compounds represented by the general formula [I] or salts thereof, Compounds defined by above (6c) in the compounds represented by the general formula [I] or salts thereof, Compounds defined by above (7c) in the compounds represented by the general formula [I] or salts thereof, Compounds defined by above (8c) in the compounds represented by the general formula [I] or salts thereof, Compounds defined by above (9c) in the compounds represented by the general formula [I] or salts thereof, and Compounds defined by any combination s of two or more of above (1c), (2c), (3c), (4c), (5c), (6c), (7c), (8c) and (9c) in the compounds represented by the general formula [I] or salts thereof.

The most preferred examples of the present compound are compounds wherein the group(s) is (are) the followings in the compounds represented by the general formula [I] or salts thereof;

(1d) $R^1$ is a group selected from hydrogen and methyl; and/or
(2d) $R^2$ is hydrogen; and/or
(3d) $R^3$ is a group selected from 2-cyclopentylethyl, 2-cyclohexylethyl, 2-(cyclohexen-1-yl)ethyl, 2-(1-adamantyl)ethyl, phenethyl, 3-phenylpropyl and 4-fluorophenethyl; and/or
(4d) $R^4$ is hydrogen; and/or
(5d) $R^5$ is hydrogen; and/or
(6d) $R^6$ is a group selected from 3-pyridyl and 4-pyridyl; and/or
(7d) $A^1$ is ethylene; and/or
(8d) $A^2$ is a group selected from methylene, ethylene and propylene.

Namely,
Compounds defined by above (1d) in the compounds represented by the general formula [I] or salts thereof,
Compounds defined by above (2d) in the compounds represented by the general formula [I] or salts thereof,
Compounds defined by above (3d) in the compounds represented by the general formula [I] or salts thereof,
Compounds defined by above (4d) in the compounds represented by the general formula [I] or salts thereof,
Compounds defined by above (5d) in the compounds represented by the general formula [I] or salts thereof,
Compounds defined by above (6d) in the compounds represented by the general formula [I] or salts thereof,
Compounds defined by above (7d) in the compounds represented by the general formula [I] or salts thereof,
Compounds defined by above (8d) in the compounds represented by the general formula [I] or salts thereof, and
Compounds defined by any combinations of two or more of above (1d), (2d), (3d), (4d), (5d), (6d), (7d) and (8d) in the compounds represented by the general formula [I] or salts thereof.

The present compounds can be compounds wherein thiol, hydroxy, or nitrogen of the nonaromatic heterocycle or the aromatic heterocycle is protected with the protecting group or salts thereof in the above-mentioned preferred examples, more preferred examples, further preferred examples and most preferred examples of the compound or the salts thereof. In the compounds wherein the thiol is protected with the protecting group or the salts thereof, $R^1$ is the protecting group of the thiol. In particular, compounds wherein thiol is protected with acetyl or salts thereof are preferable.

A typical synthesis route scheme of the present compound is shown below.

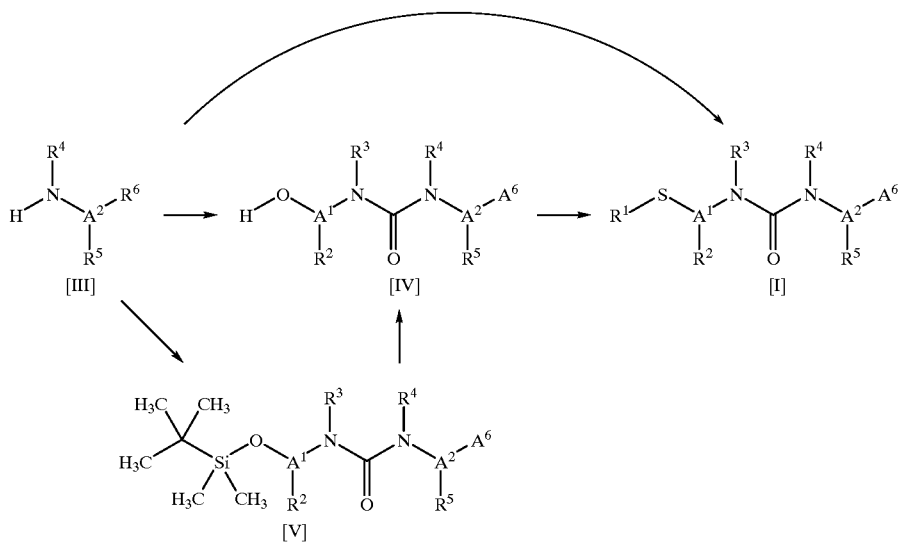

The present compound [I] can be synthesized through various synthesis routes, for example, as shown in the above reaction route scheme. Each route is as follows. However, these routes exemplify typical routes and do not show all methods. Detailed synthesis methods are described in Examples later.

Route A) [III]→[IV]→[I]
Route B) [III]→[V]→[IV]→[I]
Route C) [III]→[I]

The synthesis methods of these routes are described in more detail below.

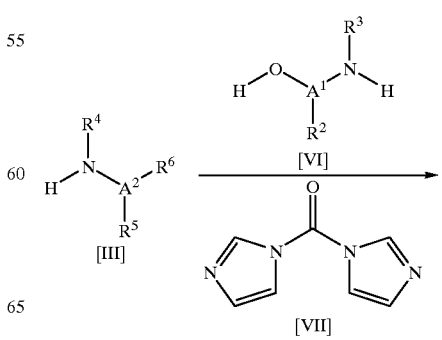

-continued

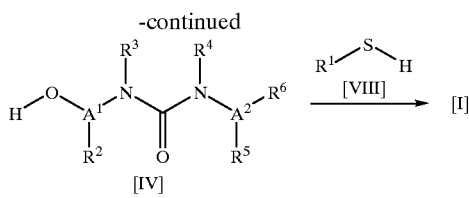

The compound [III] is reacted with the amino alcohol derivative [VI] in the presence of the condensation agent (for example, 1,1'-carbonyldiimidazole [VII]) to convert it into the compound represented by the formula [IV]. Then, the compound [IV] is condensed with the thiol derivative [VIII] by Mitsunobu reaction to give the present compound [I].

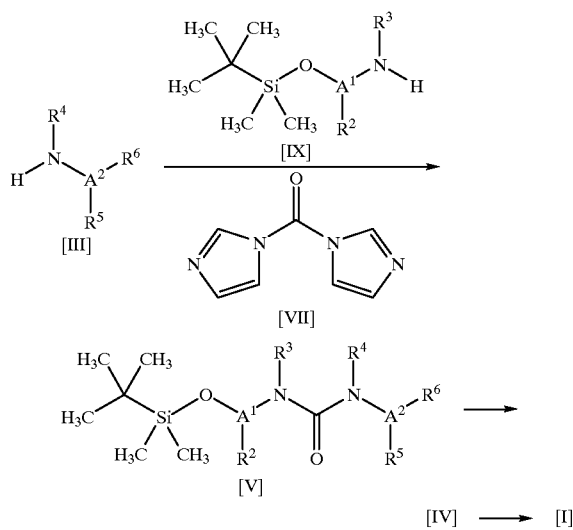

The compound [III] is reacted with the compound represented by the formula [IX] in the presence of the condensation agent (for example, 1,1'-carbonyldiimidazole [VII]) to convert it into the compound represented by the formula [V]. Then, the compound [V] is deprotected with TBAF (tetra-n-butylammonium fluoride) to give the compound [IV]. Then, the present compound [I] is obtained in the same manner as by the route A).

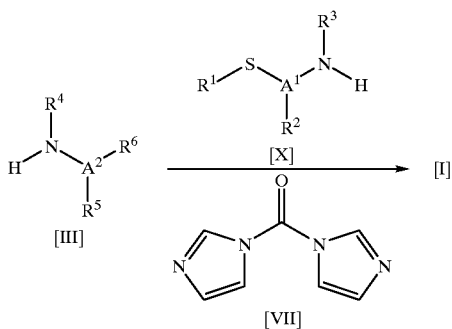

The compound [III] is reacted with the compound represented by the formula [X] in the presence of the condensation agent (for example, 1,1'-carbonyldiimidazole [VII]) to give the present compound [I].

In the above-mentioned synthesis methods, when the reactant has a thiol, hydroxy or amino group in its molecule, these groups can be protected with suitable protecting groups, if necessary, and these protecting groups can also be removed by the conventional method after react ion. When the reactant has a carboxyl group in its molecule, the carboxyl group can be esterified, if necessary, and the ester can also be converted into a carboxylic acid by hydrolysis or the like.

In the present compound, when $R^2$ joins with sulfur adjacent to $A^1$ to form a thiolactone ring, the present compound can also be synthesized by the following methods other than the above-mentioned routes. Namely, when $R^2$ is carboxyl and $R^1$ is hydrogen in the formula [I], the thiolactone ring can also be synthesized by condensing these groups.

The compounds obtained by the above-mentioned methods can be converted into the above-mentioned salts by the conventional method.

The chemical structural feature of the present compounds is that the compounds have urea structure as basic structure and have a sulfur atom in one side chain and a nitrogen aromatic heterocycle in the other side chain respectively. Few studies of such drugs having the urea structure as basic skeleton have been reported. Moreover, no drug having a sulfur atom in a side chain has hitherto practically been reported. Limiting drugs to those having the TNF-α production inhibitory effects, which is an object of the present invention, no drug having a chemical structure similar to the present compound is known at all.

The present inventors precisely studied the synthesis of the compounds having the urea structure as basic structure which thus had been hitherto hardly studied, prepared the many novel compounds, found that these novel compounds have the excellent TNF-α production inhibitory effects, and completed the present invention. The present compounds exhibit the effects both in state where the sulfur atom in the side chain joins with various groups (represented by $R^1$ in the formula [I] except for hydrogen) and in the state where the sulfur atom takes the form of SH ($R^1$ in the formula [I] is hydrogen). When $R^1$ plays a role as a protecting group of the SH group, the protecting group is sometimes removed by hydrolysis and the like and the resulting form of SH exhibits the effects. When the present compounds contain a carboxylate in their molecule, the present compounds exhibit the effects even in the ester state. The ester linkage is sometimes subject to hydrolysis and the like and the resulting form of a carboxylic acid exhibits the effects. When the present compounds contain a group which is converted into a free hydroxy or amino group, the present compounds can be administered in state where these groups are protected with suitable protecting groups. The present compounds can be administered in state where these protecting groups are removed.

The TNF-α production inhibitory effects of the present compounds were examined in order to study utility of the present compounds. Details will be described in the item of pharmacological test below. Studying in vivo inhibitory effects on liberation of TNF-α caused by stimulation of lipopolysaccharide (LPS), the present compounds exhibited the excellent TNF-α production inhibitory effects.

TNF-α production is known to be closely related to crises of autoimmune diseases such as rheumatoid arthritis, Crohn's disease and systemic lupus erythematosus, cachexia, acute infectious disease, allergy, pyrexia, anemia, diabetes and the like. Compounds which inhibit its production like the present compounds may be used as an active drug in method(s) of treating these various diseases.

The present compound can be administered orally or parenterally. Examples of dosage forms are tablets, capsules, granules, powders, injections and the like. The present compound can be formulated with a carrier into preparations by the conventional methods. For example, oral preparations such as tablets, capsules, granules and powders can be produced by adding optionally diluents such as lactose, crystalline cellulose, starch and vegetable oil; lubricants such as magnesium stearate and talc; binders such as hydroxypropylcellulose and polyvinyl pyrrolidone; disintegrator such as calcium carboxymethylcellulose or low-substituted hydroxypropylmethylcellulose; coating agent such as hydroxypropylmethylcellulose, macrogol or silicone resin; or film forming agent such as gelatin film.

The dosage of the present compound can be selected suitably according to the human patient's symptom and age; and the dosage form and the like. The present compound can be administered once to several times per day with a daily dose of 0.1 to 5000 mg, preferably 1 to 1000 mg, preferably for an oral preparation.

Examples of preparations and formulations and results of pharmacological test of the present invention are shown below. These examples do not limit the scope of the invention, but are intended to make the invention more clearly understandable.

Preparation of Compounds

REFERENCE EXAMPLE 1

3-(4-Pyridyl)propylamine (Reference Compound No. 1-1)

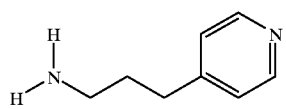

N-[3-(4-Pyridyl)propyl]phthalimide (799 mg) and hydrazine monohydrate (600 mg) are dissolved in methanol (15 ml), and the solution is refluxed for four hours. After cooling, the reaction mixture is concentrated under reduced pressure, and chloroform is added to the residue. The organic layer is washed with a saturated aqueous sodium carbonate solution and saturated brine successively, dried over anhydrous sodium sulfate and concentrated under reduced pressure to give the titled compound (Reference compound No. 1-1, 366 mg).
(Reference Compound No. 1-1)
  IR(Film,cm$^{-1}$) 3359, 2932, 2859, 1602, 1558, 1416, 1219, 1069, 994, 893, 835, 798, 755

The following compounds are obtained by a method similar to Reference Example 1.
(RS)-1-(4-Pyridyl)ethylamine (Reference compound No. 1-2)
3-(2-Pyridyl)propylamine (Reference compound No. 1-3)
  IR(Film,cm$^{-1}$) 2980, 2935, 1707, 1592, 1110
3-(3-Pyridyl)propylamine (Reference compound No. 1-4)
  IR(Film,cm$^{-1}$) 3362, 3284, 2931, 2858, 1575, 1478, 1423
3-(1-Pyrrolyl)propylamine (Reference compound No. 1-5)
  IR(Film,cm$^{-1}$) 3368, 3295, 3097, 2931, 2868, 1500, 1449, 1352, 1280, 1090, 1060
(2-Methyl-4-thiazolyl)methylamine (Reference compound No. 1-6)
  IR(Film,cm$^{-1}$) 3363, 3290, 2922, 2849, 1600, 1525, 1478, 1440, 1185,
5-(4-Pyridyl)pentylamine (Reference compound No. 1-7)
  IR(Film,cm$^{-1}$) 3350, 2932, 2858, 1603, 1536, 1484, 1416, 1391, 1316, 1220, 804
(4-Pyrimidinyl)methylamine (Reference compound No. 1-8)
  IR(Film,cm$^{-1}$) 3362, 1658, 1641, 1586, 1551, 1389

REFERENCE EXAMPLE 2

N-(2-Cyclohexylethyl)-(4-pyridyl)methylamine (Reference Compound No. 2-1)

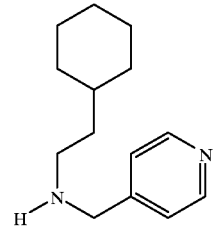

To a solution of 2-cyclohexylethyl bromide (1.50 g) in ethanol (16 ml) are added 4-picolylamine (1.00 g), anhydrous potassium carbonate (1.32 g) and sodium iodide (3.49 g), and the mixture is refluxed for 17 hours with stirring. Water is added to the reaction mixture, and the whole is extracted with ether. The organic layer is washed with saturated brine, dried over anhydrous magnesium sulfate and concentrated under reduced pressure. The resulting residue is purified by silica gel column chromatography to give the titled compound (Reference compound No. 2-1, 0.68 g).

The following compound is obtained by a method similar to Reference Example 2.
N-Phenethyl-3-(4-pyridyl)propylamine (Reference compound No. 2-2)
  IR(Film,cm$^{-1}$) 3025, 2933, 1602, 1495, 1453, 1415

REFERENCE EXAMPLE 3

4-(4-Pyridyl)butylamine (Reference Compound No. 3-1)

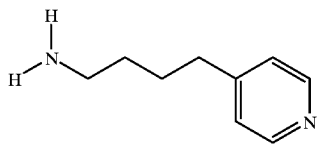

Lithium aluminum hydride (370 mg) is suspended in anhydrous ether (14 ml) under a nitrogen atmosphere and ice cooling, and a solution of 4-(4-pyridyl)butyronitrile (705 mg) in anhydrous ether (10 ml) is added dropwise to the suspension. The mixture is stirred at room temperature for 2.5 hours. Anhydrous sodium sulfate is added to the reaction mixture under ice cooling, and water (0.5 ml) is added drop by drop thereto. Then, tetrahydrofuran is added thereto, and insoluble matter is filtered out. The filtrate is concentrated under reduced pressure to give the titled compound (Reference compound No. 3-1, 827 mg).
(Reference Compound No. 3-1)
  IR(Film,cm$^{-1}$) 3284, 3068, 3024, 2932, 2858, 1602, 1557, 1458, 1415, 1219, 1069, 993, 804, 752

REFERENCE EXAMPLE 4

2-(Aminomethyl)benzothiazole Hydrochloride (Reference Compound No. 4-1)

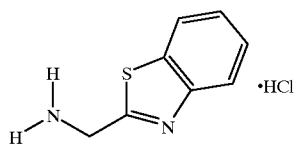

1) 2-Aminothiophenol (1.2 ml) is added to a solution of 2-phenyl-4,5-dihydro-1,3-oxazol-5-one (1.8 g) in acetic acid (14 ml), and the mixture is stirred for one hour while heating it at 40° C. Water is added to the reaction mixture, and the resulting precipitate is filtered off to give 2-(benzoylaminomethyl)benzothiazole (0.75 g) as crystals.

mp 139.5~142.0° C.

IR(KBr,cm$^{-1}$) 3270, 1639, 1536, 1522, 1317

2) Concentrated hydrochloric acid (5.8 ml) is added to a solution of 2-(benzoylaminomethyl)benzothiazole (750 mg) in dioxane (10 ml), and the mixture is refluxed for 40 hours with stirring. The reaction mixture is concentrated under reduced pressure. A 4 N aqueous sodium hydroxide solution (20 ml) is added to the residue under ice cooling to adjust pH to 10 or higher, and the whole is extracted with chloroform. The organic layer is washed with saturated brine, dried over anhydrous magnesium sulfate and concentrated under reduced pressure. The resulting residue is dissolved in methanol (10 ml), and a 4 N solution of hydrogen chloride in ethyl acetate (1.4 ml) is added thereto under ice cooling. The mixture is concentrated under reduced pressure, and the precipitate is filtered off to give the titled compound (Reference compound No. 4-1, 486 mg).

(Reference Compound No. 4-1)

mp 250° C. or higher

IR(KBr,cm$^{-1}$) 3063, 1502, 1436, 1358, 1084

REFERENCE EXAMPLE 5

2-(t-Butyldimethylsiloxy)ethylamine (Reference Compound No. 5-1)

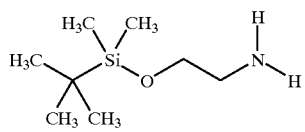

t-Butyldimethylchlorosilane (5.4 g) and imidazole (2.7 g) are added to a solution of 2-aminoethanol (2.0 ml) in anhydrous methylene chloride (65 ml), and the mixture is stirred at room temperature overnight. A 5% aqueous sodium hydrogencarbonate solution is added to the reaction mixture, and the whole is extracted with ethyl acetate. The organic layer is washed with saturated brine, dried over anhydrous magnesium sulfate and concentrated under reduced pressure to give the titled compound (Reference compound No. 5-1, 6.0 g).

(Reference Compound No. 6-1)

IR(Film,cm$^{-1}$) 2929, 2857, 1472, 1256, 1107, 836, 777

REFERENCE EXAMPLE 6

N-(2-Hydroxyethyl)-2-[4-(trifluoromethoxy)phenyl] ethylamine Hydrochloride (Reference Compound No. 6-1)

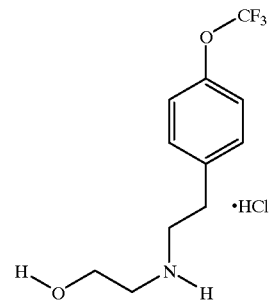

2-Bromoethanol (0.77 ml), anhydrous potassium carbonate (1.40 g) and sodium iodide (2.54 g) are added to a solution of 4-(trifluoromethoxy)phenethylamine (1.47 g) in ethanol (22 ml), and the mixture is refluxed overnight with stirring. After cooling, insoluble matter is filtered out, and the filtrate is concentrated under reduced pressure. Ether is added to the residue, and the whole is extracted. The organic layer is washed with a saturated aqueous sodium hydrogencarbonate solution and saturated brine successively, dried over anhydrous magnesium sulfate and concentrated under reduced pressure. The resulting oily matter is purified by silica gel column chromatography and then dissolved in ethyl acetate (0.1 ml). A 4 N solution of hydrogen chloride in dioxane (0.65 ml) is added thereto under ice cooling. The resulting precipitate is filtered off to give the titled compound (Reference compound No. 6-1, 437 mg) as crystals.

(Reference Compound No. 6-1)

mp 101.0~115.0° C.

IR(KBr,cm$^{-1}$) 3409, 2959, 2458, 1592, 1514, 1158

The following compounds are obtained by a method similar to Reference Example 6.

N-(2-Hydroxyethyl)-2-[4-(ethoxycarbonyl)phenyl] ethylamine hydrochloride (Reference compound No. 6-2)

mp 147.5~153.0° C.

IR(KBr,cm$^{-1}$) 3406, 2967, 2794, 2459, 1715, 1613, 1578, 1448, 1416, 1368, 1309, 1284, 1182, 1128, 1110, 1063, 1020, 852, 782, 760, 702

N-[2-(t-Butyldimethylsiloxy)ethyl]-2-(1-piperidyl) ethylamine (Reference Compound No. 6-3)

IR(Film,cm$^{-1}$) 2934, 2855, 2810, 1464, 1256, 1138, 1089, 836, 776

2-Cyclohexyl-N-(2-tetrahydrothienylmethyl)ethylamine hydrochloride (Reference compound No. 6-4)

mp 190° C.

IR(KBr,cm$^{-1}$) 2925, 2852, 2787, 2596, 1595, 1477, 1450

REFERENCE EXAMPLE 7

2-Cyclooctyl-N-(2-hydroxyethyl)ethylamine hydrochloride (Reference Compound No. 7-1)

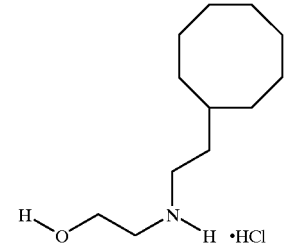

Lithium aluminum hydride (358 mg) is suspended in anhydrous ether (22 ml) under a nitrogen atmosphere and ice cooling, and a solution of N-(2-hydroxyethyl)cyclooctylacetamide (998 mg) in anhydrous ether (8 ml) is added dropwise to the suspension. The mixture is stirred at room temperature overnight. Ethyl acetate and 0.1 N hydrochloric acid are added to the reaction mixture under ice cooling until foaming stops. Then, a 4 N aqueous sodium hydroxide solution is added to the whole to basify it, and the whole is extracted with ether. The organic layer is washed with a 1 N aqueous sodium hydroxide solution and saturated brine successively, dried over anhydrous sodium sulfate and concentrated under reduced pressure. The resulting oily matter is dissolved in ether (0.5 ml), and a 4 N solution of hydrogen chloride in ethyl acetate (0.75 ml) is added thereto under ice cooling. The resulting precipitate is filtered off to give the titled compound (Reference compound No. 7-1, 500 mg) as crystals.

(Reference Compound No. 7-1)

mp 130° C.

IR(KBr,cm$^{-1}$) 3374, 2918, 2852, 1591, 1446

REFERENCE EXAMPLE 8

4-(Aminomethyl)quinoline (Reference Compound No. 8-1)

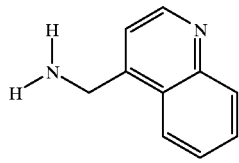

Ammonium acetate (9.8 g) is added to a solution of 4-quinolinecarboxyaldehyde (2.0 g) in methanol (50 ml), and the mixture is stirred at room temperature for three hours. Further, sodium cyanoborohydride (1.0 g) is added to the mixture, and the whole is stirred for 40 minutes. The reaction mixture is poured into water, and the whole is concentrated under reduced pressure. The concentrate is extracted with chloroform. To the organic layer is added 1 N hydrochloric acid, and the whole is extracted. A 4 N aqueous sodium hydroxide solution is added to the hydrochloric acid extract to basify it, and then the whole is extracted with chloroform. The organic layer is washed with saturated brine, dried over anhydrous magnesium sulfate and concentrated under reduced pressure. The resulting oily matter is purified by silica gel column chromatography to give the titled compound (Reference compound No. 8-1, 0.14 g).

(Reference Compound No. 8-1)

IR(Film,cm$^{-1}$) 3289, 1595, 1511, 1464, 1316

EXAMPLE 1

1-(2-Cyclohexylethyl)-1-(2-hydroxyethyl)-3-(4-pyridylmethyl)urea (Compound No. 1-1)

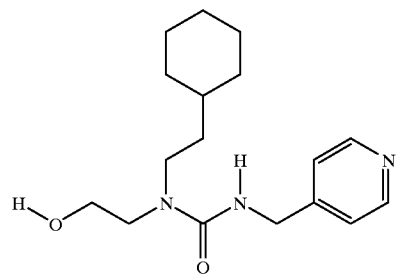

1,1'-Carbonyldiimidazole (3.60 g) is dissolved in a solution of 4-(aminomethyl)pyridine (2.00 g) in anhydrous tetrahydrofuran (62 ml) under a nitrogen atmosphere, and the mixture is stirred at room temperature for 10 minutes. N-(2-Hydroxyethyl)-2-cyclohexylethylamine hydrochloride (4.64 g) is added to the reaction mixture, and the whole is refluxed for two hours. Chloroform is added to the reaction mixture under ice cooling, and the whole is extracted. The organic layer is washed with a 10% aqueous sodium hydrogencarbonate solution, water and saturated brine successively, dried over anhydrous sodium sulfate and concentrated under reduced pressure. The resulting oily matter is purified by silica gel column chromatography to give the titled compound (Compound No. 1-1, 5.09 g).

(Compound No. 1-1)

mp 143.0~145.5° C.

IR(KBr,cm$^{-1}$) 3332, 2922, 2850, 1624, 1537, 1443, 1407, 1372, 1072

The following compounds are obtained by a method similar to Example 1.

1-(2-Cyclohexylethyl)-1-(2-hydroxyethyl)-3-[2-(4-pyridyl)ethyl]-urea (Compound No. 1-2)

IR(Film,cm$^{-1}$) 3325, 2922, 2850, 1627, 1537, 1448, 1415, 1365, 1269, 1053

1-(2-Cyclohexylethyl)-1-(2-hydroxyethyl)-3-[3-(4-pyridyl)propyl]-urea (Compound No. 1-3)

IR(Film,cm$^{-1}$) 3340, 2922, 2850, 1621, 1538, 1442, 1422, 1404, 1373, 1294, 1249, 1222, 1075, 1061

1-(2-Cyclohexylethyl)-1-(2-hydroxyethyl)-3-[(RS)-1-(4-pyridyl)-ethyl]urea (Compound No. 1-4)

IR(Film,cm$^{-1}$) 3307, 2923, 2850, 1632, 1532, 1449, 1409, 1242, 1051

1-(2-Cyclopentylethyl)-1-(2-hydroxyethyl)-3-(4-pyridylmethyl)-urea (Compound No. 1-5)

mp 122.7~125.5° C.

IR(KBr,cm$^{-1}$) 3342, 2942, 2865, 1623, 1535, 1405, 1367, 1266, 1236, 1077

1-[2-(1-Adamantyl)ethyl]-1-(2-hydroxyethyl)-3-(4-pyridylmethyl)urea (Compound No. 1-6)

1-(2-Hydroxyethyl)-1-isopentyl-3-(4-pyridylmethyl)urea (Compound No. 1-7)

IR(Film,cm$^{-1}$) 3327, 2955, 2869, 1631, 1606, 1563, 1535, 1468, 1416, 1366, 1237, 1066, 756

1-(2-Hydroxyethyl)-1-phenethyl-3-(2-pyridylmethyl)urea (Compound No. 1-8)

IR(Film,cm$^{-1}$) 3338, 2928, 1632, 1597, 1571, 1537, 1478, 1437, 1273, 1048, 751, 701

1-(2-Hydroxyethyl)-1-phenethyl-3-(3-pyridylmethyl)urea (Compound No. 1-9)

IR(Film,cm$^{-1}$) 3330, 1626, 1536, 1428, 1044

1-(2-Hydroxyethyl)-1-phenethyl-3-(4-pyridylmethyl)urea (Compound No. 1-10)

mp 98.1~99.5° C.

IR(KBr,cm$^{-1}$) 3347, 3031, 2924, 2862, 1622, 1530, 1451, 1422, 1364, 1276, 1223, 1078, 1002, 794, 771, 746, 696

1-(2-Hydroxyethyl)-1-phenethyl-3-[2-(2-pyridyl)ethyl]urea (Compound No. 1-11)

1-(2-Hydroxyethyl)-1-phenethyl-3-[2-(3-pyridyl)ethyl]urea (Compound No. 1-12)
IR(Film,cm$^{-1}$) 3325, 2930, 1628, 1538, 1235, 1049, 1030, 753

1-(2-Hydroxyethyl)-1-phenethyl-3-[2-(4-pyridyl)ethyl]urea (Compound No. 1-13)
IR(Film,cm$^{-1}$) 3329, 2930, 1625, 1537, 1496, 1453, 1416, 1365, 1273, 1233, 701

1-(2-Hydroxyethyl)-1-phenethyl-3-[3-(2-pyridyl)propyl]urea (Compound No. 1-14)
IR(Film,cm$^{-1}$) 3338, 3026, 2929, 1625, 1597, 1496, 751

1-(2-Hydroxyethyl)-1-phenethyl-3-[3-(3-pyridyl)propyl]urea (Compound No. 1-15)
IR(Film,cm$^{-1}$) 3327, 2929, 1632, 1537, 1496, 1479, 1454, 1234

1-(2-Hydroxyethyl)-1-phenethyl-3-[3-(4-pyridyl)propyl]urea (Compound No. 1-16)
IR(Film,cm$^{-1}$) 3327, 2931, 1627, 1539, 1496, 1452, 1414, 1367, 1272, 1234, 1067, 752, 702

1-(2-Hydroxyethyl)-1-(3-phenylpropyl)-3-[3-(4-pyridyl)propyl]urea (Compound No. 1-17)
IR(Film,cm$^{-1}$) 3325, 2931, 1626, 1607, 1539, 1271, 1238, 1052, 753, 700

1-(4-Fluorophenethyl)-1-(2-hydroxyethyl)-3-[3-(4-pyridyl)propyl]urea (Compound No. 1-18)
IR(Film,cm$^{-1}$) 3329, 2931, 1627, 1607, 1540, 1509, 756

1-(2-Hydroxyethyl)-3-[3-(4-pyridyl)propyl]-1-[4-(trifluoromethoxy)phenethyl]urea (Compound No. 1-19)
IR(Film,cm$^{-1}$) 3328, 2932, 1628, 1540, 1510, 1262, 759

1-[4-(Ethoxycarbonyl)phenethyl]-1-(2-hydroxyethyl)-3-[3-(4-pyridyl)propyl]urea (Compound No. 1-20)
IR(Film,cm$^{-1}$) 3330, 2932, 1714, 1609, 1538, 1446, 808, 765

1-(2-Cyclohexylethyl)-1-(2-hydroxyethyl)-3-[3-(1-pyrrolyl)propyl]urea (Compound No. 1-21)
mp 88.2~89.1° C.
IR(KBr,cm$^{-1}$) 3332, 3239, 2921, 2846, 1616, 1540, 1504, 1482, 1444, 1406, 1343, 1319, 1277, 1256, 1238, 1219, 1094

1-(2-Hydroxyethyl)-3-[2-(1-imidazolyl)ethyl]-1-phenethylurea (Compound No. 1-22)
IR(Film,cm$^{-1}$) 3114, 1626, 1537, 1454, 1232

1-(2-Cyclohexylethyl)-1-(2-hydroxyethyl)-3-[(2-methyl-4-thiazolyl)methyl]urea (Compound No. 1-23)
IR(Film,cm$^{-1}$) 3332, 2921, 2850, 1629, 1534, 1447, 1406

1-(2-Cyclohexylethyl)-1-(2-hydroxyethyl)-3-[4-(4-pyridyl)butyl]urea (Compound No. 1-24)
IR(Film,cm$^{-1}$) 3324, 2923, 2851, 1626, 1607, 1538, 1448, 1415, 1372, 1315, 1269, 1055, 1003, 753

1-(2-Cyclohexylethyl)-1-(2-hydroxyethyl)-3-[5-(4-pyridyl)pentyl]urea (Compound No. 1-25)
IR(Film,cm$^{-1}$) 3332, 2923, 2852, 1624, 1539, 1448, 1416, 1373, 1270, 1055, 754

1-(2-Cycloheptylethyl)-1-(2-hydroxyethyl)-3-(4-pyridylmethyl)-urea (Compound No. 1-26)
mp 124.0~130.5° C.
IR(KBr,cm$^{-1}$) 3343, 3038, 2922, 2850, 1622, 1608, 1534, 1496, 1458, 1302, 794, 769

1-(2-Cyclooctylethyl)-1-(2-hydroxyethyl)-3-(4-pyridylmethyl)urea (Compound No. 1-27)
mp 130.0~131.5° C.
IR(KBr,cm$^{-1}$) 3782, 3686, 3636, 3341, 2921, 2852, 1711, 1623, 1608, 1534, 1497, 1449, 1420, 1302, 1272, 787, 768

1-(2-Cyclohexylethyl)-1-(2-hydroxyethyl)-3-(4-pyrimidinyl-methyl)urea (Compound No. 1-28)
IR(Film,cm$^{-1}$) 3350, 2922, 2851, 1633, 1585, 1538, 1448, 1409, 1387, 1355

1-(2-Cyclohexylethyl)-1-(2-hydroxyethyl)-3-[2-(1-methyl-4-imidazolyl)ethyl]urea (Compound No. 1-29)

1-(2-Cyclohexylethyl)-1-(2-hydroxyethyl)-3-[2-(3-indolyl)ethyl]urea (Compound No. 1-30)
mp 147.5~149.0° C.
IR(KBr,cm$^{-1}$) 3229, 2922, 1610, 1557, 1230, 1060, 751

1-(2-Benzimidazolylmethyl)-3-(2-cyclohexylethyl)-3-(2-hydroxyethyl)urea (Compound No. 1-31)
mp 163.2~165.2° C. (decomp.)
IR(KBr,cm$^{-1}$) 3154, 2917, 2851, 1617, 1554, 1441

1-(2-Benzothiazolylmethyl)-3-(2-cyclohexylethyl)-3-(2-hydroxyethyl)urea (Compound No. 1-32)
IR(Film,cm$^{-1}$) 3323, 2922, 1634, 1536, 1448, 1410

1-(2-Cyclohexylethyl)-1-(2-hydroxyethyl)-3-(4-quinolylmethyl)-urea (Compound No. 1-33)
IR(Film,cm$^{-1}$) 3319, 2922, 2851, 1633, 1538, 1242

1-[2-(-Adamant yl)ethyl]-1-(2-hydroxyethyl)-3-[3-(1-imidazolyl)propyl]urea (Compound No. 1-34)
mp 111~125° C.
IR(KBr,cm$^{-1}$) 3378, 3216, 3117, 2899, 2845, 1626, 1596, 1542, 1482, 1450, 1409

EXAMPLE 2

1-[2-(t-Butyldimethylsiloxy)ethyl]-1-[2-(1-cyclohexenyl)ethyl]-3-(4-pyridylmethyl)urea (Compound No. 2-1)

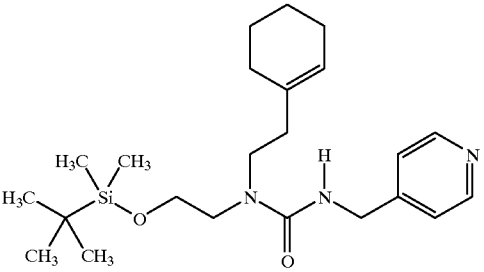

4-(Aminomethyl)pyridine (0.73 g) and 1,1'-carbonyldiimidazole (1.23 g) are suspended in anhydrous tetrahydrofuran (12 ml) under a nitrogen atmosphere, and the suspension is stirred at room temperature for 30 minutes. N-[2-(t-Butyldimethylsiloxy)ethyl]-2-(1-cyclohexenyl)ethylamine (1.88 g) is added to the reaction mixture, and the whole is refluxed for 1.5 hours. After standing, water is added to the reaction mixture, and the whole is extracted with ethyl acetate. The organic layer is washed with saturated brine, dried over anhydrous magnesium sulfate and concentrated under reduced pressure. The resulting oily matter is purified by silica gel column chromatography to give the titled compound (Compound No. 2-1, 3.01 g).
(Compound No. 2-1)
IR(Film,cm$^{-1}$) 3350, 2928, 2856, 1633, 1601, 1563, 1530, 1472, 1414

The following compounds are obtained by a method similar to Example 2.

1-[2-(t-Butyldimethylsiloxy)ethyl]-1-[2-(1-piperidyl)ethyl]-3-(4-pyridylmethyl)urea (Compound No. 2-2)
IR(Film,cm$^{-1}$) 3342, 2932, 2855, 2803, 1644, 1536, 1471, 1256, 1104, 836, 776

1-[2-(t-Butyldimethylsiloxy)ethyl]-1-[2-(4-pyridyl)ethyl]-3-[3-(4-pyridyl)propyl]urea (Compound No. 2-3)
IR(Film,cm$^{-1}$) 3351, 2930, 2857, 1634, 1603, 1535, 1470, 1415, 1363, 1252, 1103, 928, 836, 779

1-[2-(t-Butyldimethylsiloxy)ethyl]-3-(2-cyclohexylethyl)-3-(4-pyridylmethyl)urea (Compound No. 2-4)

EXAMPLE 3

1-[2-(1-Cyclohexenyl)ethyl]-1-(2-hydroxyethyl)-3-(4-pyridylmethyl)urea (Compound No. 3-1)

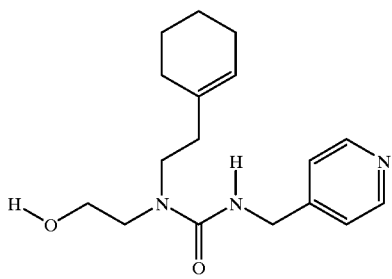

1-[2-(t-Butyldimethylsiloxy)ethyl]-1-[2-(1-cyclohexenyl)ethyl]-3-(4-pyridylmethyl)urea (Compound No. 2-1, 3.01 g) and a 1 M solution of tetra-n-butylammonium fluoride in tetrahydrofuran (8.0 ml) are dissolved in anhydrous tetrahydrofuran (18 ml) under a nitrogen atmosphere, and the mixture is stirred at room temperature overnight. Water is added to the reaction mixture, and the whole is extracted with ethyl acetate and chloroform. The organic layer is washed with saturated brine, dried over anhydrous magnesium sulfate and concentrated under reduced pressure. The precipitated crystals are filtered off to give the titled compound (Compound No. 3-1, 1.58 g).
(Compound No. 3-1)
mp 117.0~118.0° C.
IR(KBr,cm$^{-1}$) 3347, 2925, 1622, 1531, 1420, 1403, 1365

The following compounds are obtained by a method similar to Example 3.

1-(2-Hydroxyethyl)-1-[2-(1-piperidyl)ethyl]-3-(4-pyridylmethyl)urea (Compound No. 3-2)
IR(Film,cm$^{-1}$) 3316, 2935, 1636, 1531, 1470, 1415, 1362, 1272, 1042, 755

1-(2-Hydroxyethyl)-1-[2-(4-pyridyl)ethyl]-3-[3-(4-pyridyl)propyl]urea (Compound No. 3-3)

1-(2-Cyclohexylethyl)-3-(2-hydroxyethyl)-1-(4-pyridylmethyl)urea (Compound No. 3-4)
IR(Film,cm$^{-1}$) 3349, 2922, 2850, 1628, 1536, 1447, 1415, 1266

EXAMPLE 4

1-[2-(Acetylthio)ethyl]-1-(2-cyclohexylethyl)-3-(4-pyridylmethyl)urea (Compound No. 4-1)

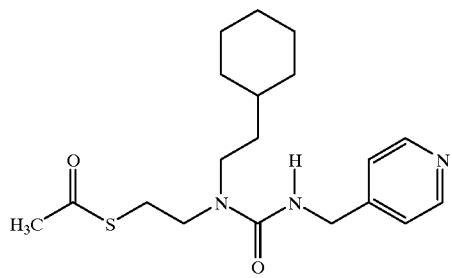

1-(2-Cyclohexylethyl)-1-(2-hydroxyethyl)-3-(4-pyridylmethyl)urea (Compound No. 1-1, 550 mg) and triphenylphosphine (944 mg) are dissolved in anhydrous tetrahydrofuran (4 ml) under a nitrogen atmosphere, and the solution is stirred under sodium chloride-ice cooling for 30 minutes. Diisopropyl azodicarboxylate (0.71 ml) and thioacetic acid (0.26 ml) are added dropwise successively to the solution while keeping temperature at 5° C. or lower. The mixture is stirred for 15 minutes, a 10% aqueous sodium hydrogencarbonate solution (30 ml) is added to the reaction mixture, and the whole is extracted with ethyl acetate. The organic layer is washed with saturated brine, dried over anhydrous magnesium sulfate and concentrated under reduced pressure. The resulting oily matter is purified by silica gel column chromatography to give the titled compound (Compound No. 4-1). (Compound No. 4-1)
IR(Film,cm$^{-1}$) 3348, 2922, 2850, 1692, 1633, 1602, 1531, 1413, 1358, 1294, 1223, 1134, 1108

The following compounds are obtained by a method similar to Example 4.

1-[2-(Acetylthio)ethyl]-1-(2-cyclohexylethyl)-3-[2-(4-pyridyl)ethyl]urea (Compound No. 4-2)
IR(Film,cm$^{-1}$) 3351, 2923, 2850, 1772, 1711, 1633, 1538, 1434, 1394, 755, 720

1-[2-(Acetylthio)ethyl]-1-(2-cyclohexylethyl)-3-[3-(4-pyridyl)propyl]urea (Compound No. 4-3)
mp 70° C.
IR(KBr,cm$^{-1}$) 3346, 3066, 3027, 2923, 2840, 1705, 1627, 1604, 1540, 1485, 1455, 1442, 1424, 1416, 1403, 1358, 1314, 1294, 1264, 1245, 1225, 1186, 1167, 1144, 1119

1-[2-(Acetylthio)ethyl]-1-(2-cyclohexylethyl)-3-[1-(4-pyridyl)ethyl]urea (Compound No. 4-4)
IR(Film,cm$^{-1}$) 2976, 2922, 2850, 1727, 1690, 1632, 1600, 1526, 1448, 1407, 1374, 1296, 1220, 1135, 1107

1-[2-(Acetylthio)ethyl]-1-(2-cyclopentylethyl)-3-(4-pyridylmethyl)urea (Compound No. 4-5)
IR(Film,cm$^{-1}$) 3349, 2946, 1692, 1632, 1602, 1531, 1414, 1295, 1135

1-[2-(Acetylthio)ethyl]-1-[2-(1-adamantyl)ethyl]-3-(4-pyridylmethyl)urea (Compound No. 4-6)

1-[2-(Acetylthio)ethyl]-1-isopentyl-3-(4-pyridylmethyl)urea (Compound No. 4-7)
IR(Film,cm$^{-1}$) 3350, 2955, 2870, 1693, 1633, 1601, 1563, 1531, 1468, 1415, 1357, 1296, 1237, 1137, 948

1-[2-(Acetylthio)ethyl]-1-phenethyl-3-(2-pyridylmethyl)urea (Compound No. 4-8)
IR(Film,cm$^{-1}$) 3383, 2930, 1688, 1636, 1593, 1532, 1436, 1355, 1137, 752

1-[2-(Acetylthio)ethyl]-1-phenethyl-3-(3-pyridylmethyl)urea (Compound No. 4-9)
IR(Film,cm$^{-1}$) 3370, 2930, 1689, 1633, 1536, 1290

1-[2-(Acetylthio)ethyl]-1-phenethyl-3-(4-pyridylmethyl)urea (Compound No. 4-10)
IR(Film,cm$^{-1}$) 3360, 3026, 2930, 1690, 1633, 1602, 1562, 1533, 1496, 1454, 1415, 1357, 1291, 1224, 1136, 951, 751, 701

1-[2-(Acetylthio)ethyl]-1-phenethyl-3-[2-(2-pyridyl)ethyl]urea (Compound No. 4-11)

1-[2-(Acetylthio)ethyl]-1-phenethyl-3-[2-(3-pyridyl)ethyl]urea (Compound No. 4-12)
IR(Film,cm$^{-1}$) 3390, 1688, 1633, 1535, 1479, 1136, 752

1-[2-(Acetylthio)ethyl]-1-phenethyl-3-[2-(4-pyridyl)ethyl]urea (Compound No. 4-13)
IR(Film,cm$^{-1}$) 3390, 1685, 1636, 1604, 1534, 1497, 1416, 1356, 1291, 1221, 1136, 752, 701

1-[2-(Acetylthio)ethyl]-1-phenethyl-3-[3-(2-pyridyl)propyl]urea (Compound No. 4-14)
IR(Film,cm$^{-1}$) 3399, 3062, 2931, 1682, 1633, 1568, 1537, 1476, 751

1-[2-(Acetylthio)ethyl]-1-phenethyl-3-[3-(3-pyridyl)propyl]urea (Compound No. 4-15)
IR(Film,cm$^{-1}$) 3391, 2930, 1688, 1632, 1536, 1479, 1290, 1135

1-[2-(Acetylthio)ethyl]-1-phenethyl-3-[3-(4-pyridyl)propyl]
urea (Compound No. 4-16)
IR(Film,cm$^{-1}$) 3391, 2933, 1688, 1632, 1603, 1536, 1497,
1453, 1415, 1356, 1290, 1220, 1136, 994, 952, 751, 701

1-[2-(Acetylthio)ethyl]-1-(3-phenylpropyl)-3-[3-(4-pyridyl)
propyl]urea (Compound No. 4-17)
IR(Film,cm$^{-1}$) 3391, 2935, 1688, 1632, 1537, 1496, 1415,
1294, 1219, 952, 753, 700

1-[2-(Acetylthio)ethyl]-1-(4-fluorophenethyl)-3-[3-(4-pyridyl)propyl]urea (Compound No. 4-18)
IR(Film,cm$^{-1}$) 3392, 2933, 1686, 1636, 1603, 1509, 1220

1-[2-(Acetylthio)ethyl]-3-[3-(4-pyridyl)propyl] 1-[4-(trifluoromethoxy)phenethyl]urea (Compound No. 4-19)
IR(Film,cm$^{-1}$) 3394, 2935, 1690, 1634, 1604, 1536, 1261

1-[2-(Acetylthio)ethyl]-1-[4-(ethoxycarbonyl)phenethyl]-3-[3-(4-pyridyl)propyl]urea (Compound No. 4-20)
IR(Film,cm$^{-1}$) 3396, 2933, 1714, 1690, 1608, 1534, 1415, 765, 706

1-[2-(Acetylthio)ethyl]-1-(2-cyclohexylethyl)-3-[3-(1-pyrrolyl)propyl]urea (Compound No. 4-21)
IR(Film,cm$^{-1}$) 3366, 2923, 2850, 1690, 1632, 1533, 1447, 1404, 1355, 1282, 1218, 1136, 1090

1-[2-(Acetylthio)ethyl]-3-[2-(1-imidazolyl)ethyl]-1-phenethylurea (Compound No. 4-22)
IR(Film,cm$^{-1}$) 3387, 2937, 1688, 1640, 1537, 1289

1-[2-(Acetylthio)ethyl]-1-(2-cyclohexylethyl)-3-[(2-methyl-4-thiazolyl)methyl]urea (Compound No. 4-23)

1-[2-(Acetylthio)ethyl]-1-(2-cyclohexylethyl)-3-[4-(4-pyridyl)butyl]urea (Compound No. 4-24)
IR(Film,cm$^{-1}$) 3350, 2922, 2851, 1690, 1632, 1603, 1534, 1448, 1414, 1355, 1293, 1219, 1137, 951, 754

1-[2-(Acetylthio)ethyl]-1-(2-cyclohexylethyl)-3-[5-(4-pyridyl)pentyl]urea (Compound No. 4-25)
IR(Film,cm$^{-1}$) 3354, 2924, 2852, 1689, 1633, 1536, 1448, 1415, 1356, 1293, 1218, 1136, 993

1-[2-(Acetylthio)ethyl]-1-(2-cycloheptylethyl)-3-(4-pyridylmethyl)urea (Compound No. 4-26)

1-[2-(Acetylthio)ethyl]-1-(2-cyclooctylethyl)-3-(4-pyridylmethyl)urea Compound No. 4-27)
IR(Film,cm$^{-1}$) 3350, 2919, 2854, 1693, 1633, 1602, 1563, 1531, 1446, 1415, 755

1-[2-(Acetylthio)ethyl]-1-(2-cyclohexylethyl)-3-(4-pyrimidinylmethyl)urea (Compound No. 4-28)
IR(Film,cm$^{-1}$) 3369, 2922, 2850, 1691, 1632, 1582, 1530, 1448, 1386, 1353

1-[2-(Acetylthio)ethyl]-1-(2-cyclohexylethyl)-3-[2-(1-methyl-4-imidazolyl)ethyl]urea (Compound No. 4-29)
IR(Film,cm$^{-1}$) 3350, 2922, 2850, 1692, 1639, 1536, 1448, 1407, 1355, 1295, 1226, 1137, 951, 753

1-[2-(Acetylthio)ethyl]-1-(2-cyclohexylethyl)-3-[2-(3-indolyl)ethyl]urea (Compound No. 4-30)
IR(Film,cm$^{-1}$) 3400, 3256, 2923, 2850, 1683, 1633, 1537, 1454, 743

1-[2-(Acetylthio)ethyl]-3-(2-benzimidazolylmethyl)-1-(2-cyclohexylethyl)urea (Compound No. 4-31)
IR(Film,cm$^{-1}$) 3338, 2923, 2851, 1693, 1633, 1537, 1446, 1296, 1272, 751

1-[2-(Acetylthio)ethyl]-3-(2-benzothiazolylmethyl)-1-(2-cyclohexylethyl)urea (Compound No. 4-32)
IR(Film,cm$^{-1}$) 3361, 2922, 1689, 1639, 1533

1-[2-(Acetylthio) ethyl]-1-[2-(1-cyclohexenyl) ethyl]-3-(4-pyridylmethyl)urea (Compound No. 4-33)

1-[2-(Acetylthio)ethyl]-1-[2-(1-piperidyl)ethyl]-3-(4-pyridylmethyl)urea (Compound No. 4-34)
IR(Film,cm$^{-1}$) 3350, 2934, 2851, 2803, 1691, 1649, 1600, 1530, 1414, 1355, 1274, 1114, 994, 952, 758

1-[2-(Acetylthio)ethyl]-1-[2-(4-pyridyl)ethyl]-3-[3-(4-pyridyl)propyl]urea (Compound No. 4-35)

IR(Film,cm$^{-1}$) 3391, 2931, 1688, 1632, 1603, 1537, 1416, 1357, 1294, 1220, 1136

1-[2-(Acetylthio)ethyl]-3-(2-cyclohexylethyl)-3-(4-pyridylmethyl)urea (Compound No. 4-36)
IR(Film,cm$^{-1}$) 3350, 2922, 2850, 1693, 1633, 1601, 1531, 1414, 1252, 1135

1-[2-(Acetylthio)ethyl]-1-(2-cyclohexylethyl)-3-(4-quinolylmethyl)urea (Compound No. 4-37)

1-[2-(Acetylthio)ethyl]-1-[2-(1-adamantyl)ethyl]-3-[3-(1-imidazolyl)propyl]urea (Compound No. 4-38)
IR(Film,cm$^{-1}$) 3392, 3109, 2902, 2845, 1690, 1633, 1534, 1449, 1405

EXAMPLE 5

1-(2-Cyclohexylethyl)-1-[2-(methylthio)ethyl]-3-[3-(4-pyridyl)propyl]urea (Compound No. 5-1)

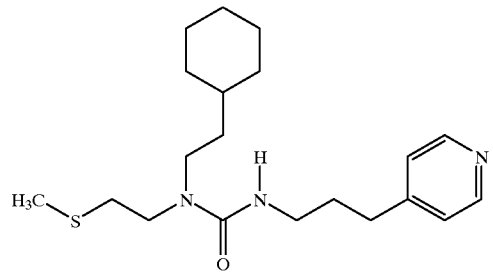

4-(3-Aminopropyl)pyridine (Reference compound No. 1-1, 101 mg) and 1,1'-carbonyldiimidazole (131 mg) are suspended in anhydrous tetrahydrofuran (10 ml) under a nitrogen atmosphere, and the suspension is stirred at room temperature for 30 minutes. 2-Cyclohexyl-N-[2-(methylthio)ethyl]ethylamine (149 mg) is added to the mixture, and the whole is refluxed for two hours. Water is added to the reaction mixture under ice cooling, and the whole is extracted with ethyl acetate. The organic layer is washed with saturated brine, dried over anhydrous magnesium sulfate and concentrated under reduced pressure. The resulting oily matter is purified by silica gel column chromatography to give the titled compound (Compound No. 5-1, 212 mg).
(Compound No. 5-1)
IR(Film,cm$^{-1}$) 3346, 2922, 2851, 1627, 1535, 1447, 1415, 1294, 1221

The following compounds are obtained by a method similar to Example 5.

1 (2-Cyclohexylethyl)-1-[2-(methylthio)ethyl]-3-(4-pyridylmethyl)urea (Compound No. 5-2)
mp 65.5~67.3° C.
IR(KBr,cm$^{-1}$) 3331, 2923, 1630, 1600, 1534, 1413

1-[(2RS)-2-(Benzylthio)-3-methylbutyl]-1-phenethyl-3-[3-(4-pyridyl)propyl]urea (Compound No. 5-3)
IR(Film,cm$^{-1}$) 3350, 3062, 3026, 2957, 2868, 1628, 1603, 1530, 1495, 1453, 1415, 1383, 1364, 1297, 1242, 1220

1-(2-Cyclohexylethyl)-3-(4-pyridylmethyl)-1-[(2RS)-2-tetrahydrothienyl]methylurea (Compound No. 5-4)
mp 95.2~96.5° C.
IR(KBr,cm$^{-1}$) 3301, 2925, 2851, 1626, 1602, 1563, 1522, 1445, 1412

1-[(3RS)-2-Oxo-3-tetrahydrothienyl]-3-phenethyl-3-[3-(4-pyridyl)propyl]urea (Compound No. 5-5)
IR(Film,cm$^{-1}$) 2939, 1704, 1633, 1530, 1305, 1220

1,1'-[(1R,1'R)-1,1'-Bis(methoxycarbonyl)-2,2'-(dithio)
diethyl]-3,3'-bis[3-(4-pyridyl)propyl]-3,3'-diphenethyldiurea (Compound No. 5-6)

EXAMPLE 6

1-[(R)-2-(Acetylthio)-1-(methoxycarbonyl)ethyl]-3-phenethyl-3-[3-(4-pyridyl)propyl]urea (Compound No. 6-1)

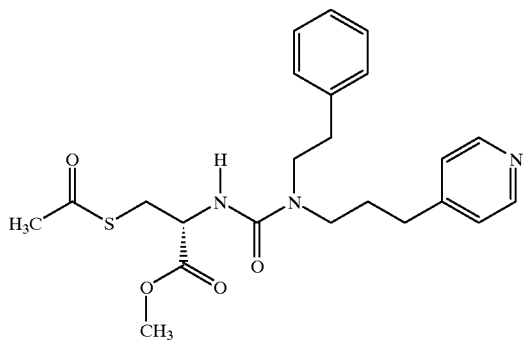

1,1'-[(1R,1'R)-1,1'-Bis(methoxycarbonyl)-2,2'-(dithio)diethyl]-3,3'-bis[3-(4-pyridyl)propyl]-3,3'-diphenethyldiurea (Compound No. 5-6, 1.01 g) is dissolved in acetone (10 ml) under a nitrogen atmosphere. Then, water (2.5 ml) and tri-n-butylphosphine (0.69 ml) are added to the solution, and the mixture is stirred at room temperature for 4.5 hours. Triethylamine (0.44 ml) and acetic anhydride (0.30 ml) are added to the reaction mixture under a nitrogen atmosphere, and the whole is stirred at room temperature for 20 minutes. The reaction mixture is concentrated under reduced pressure, and 1 N hydrochloric acid is added to the residue to acidify it. The aqueous layer is washed with ether. A 1 N aqueous sodium hydroxide solution is added to the aqueous layer under ice cooling to basify it weakly, and the whole is extracted with ethyl acetate. The organic layer is washed with saturated brine, dried over anhydrous sodium sulfate and concentrated under reduced pressure. The resulting oily matter is purified by silica gel column chromatography to give the titled compound (Compound No. 6-1, 0.50 g).

(Compound No. 6-1)

$[\alpha]_D^{20}$ −40.9° (c=1.0, methanol)

IR(Film,cm$^{-1}$) 2950, 1744, 1693, 1643, 1524, 1204, 1136

EXAMPLE 7

1-(2-Cyclohexylethyl)-1-(2-mercaptoethyl)-3-[3-(4-pyridyl)propyl]urea (Compound No. 7-1)

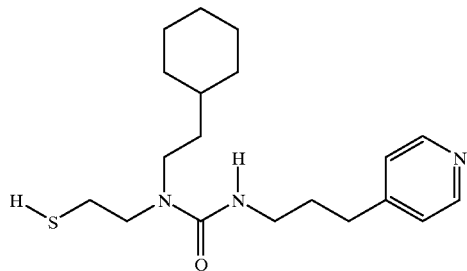

1-(2-Cyclohexylethyl)-1-(2-(acetylthio)ethyl)-3-[3-(4-pyridyl)propyl]urea (Compound No. 4-3, 200 mg) is dissolved in methanol (1.0 ml) under a nitrogen atmosphere. Then, a 1 N aqueous sodium hydroxide solution (0.5 ml) is added dropwise thereto, and the mixture is stirred at room temperature for 20 minutes. To the reaction mixture is added 1 N hydrochloric acid to adjust it to pH 7. After concentration under reduced pressure, a 10% aqueous sodium hydrogencarbonate solution (300 ml) is added to the concentrate, and the whole is extracted with ethyl acetate. The organic layer is washed with saturated brine, dried over anhydrous sodium sulfate and concentrated under reduced pressure. The resulting oily matter is purified by silica gel column chromatography to give the titled compound (Compound No. 7-1).

The following compound is obtained by a method similar to Example 7.

1-(2-Mercaptoethyl)-1-phenethyl-3-[2-(4-pyridyl)ethyl]urea (Compound No. 7-2)

EXAMPLE 8

1-[2-(Acetylthio)ethyl]-1-(2-cyclohexylethyl)-3-(4-pyridylmethyl)urea hydrochloride (Compound No. 8-1)

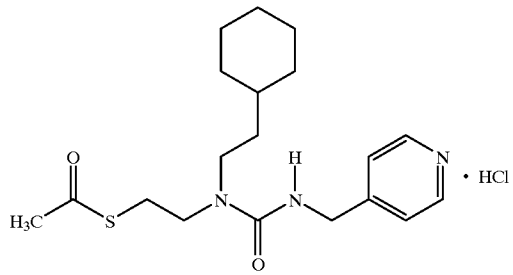

A 4 N solution of hydrogen chloride in ethyl acetate (0.45 ml) is added to a solution of i-[2-(acetylthio)ethyl]-1-(2-cyclohexylethyl)-3-(4-pyridylmethyl)urea (Compound No. 4-1, 654 mg) in chloroform (4 ml) under a nitrogen atmosphere. The mixture is stirred for one hour and then concentrated under reduced pressure, and ether is added to the concentrate. The resulting precipitate is filtered off to give the titled compound (Compound No. 8-1, 384 mg) as crystals. (Compound No. 8-1)

mp 145.0~147.0° C.

IR(KBr,cm$^{-1}$) 3285, 2923, 2851, 2428, 1692, 1637, 1605, 1530, 1498, 1407, 1367, 1298, 1138, 784

The following compounds are obtained by a method similar to Example 8.

1-[2-(Acetylthio)ethyl]-1-(2-cyclohexylethyl)-3-[3-(4-pyridyl)propyl]urea hydrochloride (Compound No. 8-2)

IR(Film,cm$^{-1}$) 3350, 2923, 2851, 1690, 1637, 1536, 1448, 1374, 1296, 1246, 1137, 754

1-[2-(Acetylthio)ethyl]-1-(2-cyclopentylethyl)-3-(4-pyridylmethyl)urea hydrochloride (Compound No. 8-3)

mp 151.4~152.6° C.

IR(KBr,cm$^{-1}$) 3271, 2948, 2864, 2428, 1689, 1637, 1606, 1526, 1498, 1407, 1367, 1138, 786

1-[2-(Acetylthio)ethyl]-1-[2-(1-adamantyl)ethyl]-3-(4-pyridylmethyl)urea hydrochloride (Compound No. 8-4)

IR(KBr,cm$^{-1}$) 3348, 2901, 2846, 2614, 1694, 1643, 1605, 1522, 1450, 1401, 1346, 1292, 1278, 1224, 1133

1-[2-(Acetylthio)ethyl]-1-phenethyl-3-(4-pyridylmethyl)urea hydrochloride (Compound No. 8-5)

mp 167.0~168.0° C. (decomp.)

IR(KBr,cm$^{-1}$) 3273, 2429, 2095, 1988, 1698, 1636, 1608, 1526, 1499, 1408, 1367, 1302, 1288, 1224, 1135, 1018, 1003, 783, 754, 706

1-[2-(Acetylthio)ethyl]-1-phenethyl-3-[3-(4-pyridyl)propyl]urea fumarate (Compound No. 8-6)

mp 110.1~115.0° C.

IR(KBr,cm$^{-1}$) 3384, 2926, 2540, 2162, 1713, 1671, 1618, 1540, 1507, 1380, 1285, 1264, 1168, 988

1-[2-(Acetylthio)ethyl]-1-(2-cyclohexylethyl)-3-[(2-methyl-4-thiazolyl)methyl]urea hydrochloride (Compound No. 8-7)
mp 121.0~124.6° C.
IR(KBr,cm$^{-1}$) 3302, 2923, 2852, 2426, 1690, 1642, 1603, 1531, 1450, 1408, 1305

1-[2-(Acetylthio)ethyl]-1-(2-cycloheptylethyl)-3-(4-pyridylmethyl)urea hydrochloride (Compound No. 8-8)
mp 138.3~140.8° C.
IR(KBr,cm$^{-1}$) 3286, 2924, 2853, 2436, 2091, 1990, 1693, 1636, 1605, 1526, 1498, 1446, 1406, 1367, 1300, 784

1-[2-(Acetylthio)ethyl]-3-(2-benzothiazolylmethyl)-1-(2-cyclohexylethyl)urea hydrochloride (Compound No. 8-9)
mp 120.3~125.4° C.
IR(KBr,cm$^{-1}$) 3270, 2922, 1694, 1637, 1518, 1442, 1293

1-[2-(Acetylthio)ethyl]-1-[2-(1-cyclohexenyl)ethyl]-3-(4-pyridylmethyl)urea hydrochloride (Compound No. 8-10)
mp 165.0~167.0° C. (decomp.)
IR(KBr,cm$^{-1}$) 3280, 3085, 2926, 2424, 2093, 1696, 1637, 1525, 1407, 1366, 1295, 1137, 1020, 784

1-(2-Cyclohexylethyl)-1-(2-mercaptoethyl)-3-[3-(4-pyridyl)propyl]urea hydrochloride (Compound No. 8-11)
IR(Film,cm$^{-1}$) 3333, 2922, 2850, 1634, 1532, 1447, 1294, 1220

EXAMPLE 9

4-[3-[2-(Acetylthio)ethyl]-3-(2-cyclohexylethyl) ureidomethyl]-1-methylpyridinium iodide (Compound No. 9-1)

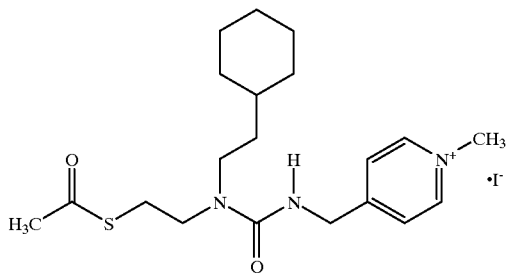

Methyl iodide (0.13 ml) is added to a solution of 1-[2-(acetylthio)ethyl]-1-(2-cyclohexylethyl)-3-(4-pyridylmethyl) urea (Compound No. 4-1, 370 mg) in acetone (2 ml). The mixture is stirred overnight and then concentrated under reduced pressure, and the resulting precipitate is filtered off to give the titled compound (Compound No. 9-1, 386 mg) as crystals.
(Compound No. 9-1)
mp 34.5~60.0° C.
IR(KBr,cm$^{-1}$) 3327, 2921, 2849, 1689, 1632, 1521, 1447, 1408, 1368, 1296, 1236, 1182, 1136, 945, 748

Formulation

General formulation examples of oral preparations and injections using the present compounds are shown below.
1) Tablet
Formulation 1 in 100 mg

| Present compound | 1 mg |
| Lactose | 66.4 mg |
| Cornstarch | 20 mg |
| Calcium carboxymethylcellulose | 6 mg |

-continued

| Hydroxypropylcellulose | 4 mg |
| Magnesium stearate | 0.6 mg |

Tablets according to the formulation as above are coated with 2 mg/tablet of a coating agent (this is a conventional coating agent such as hydroxypropylmethylcellulose, macrogol or silicone resin) to obtain desired coated tablets. (The same is applied to tablets mentioned below.) Desired tablets can be obtained by changing the amounts of the present compound and the additives appropriately.

2) Capsule
Formulation 1 in 150 mg

| Present compound | 5 mg |
| Lactose | 145 mg |

Desired capsules can be obtained by changing the mixing ratio of the present compound to lactose appropriately.

3) Injection
Formulation 1 in 10 ml

| Present compound | 10–100 mg |
| Sodium chloride | 90 mg |
| Sodium hydroxide (or hydrochloric acid) | q.s. |
| Sterile purified water | q.s. |

Desired injections can be obtained by changing the mixing ratio of the present compound to the additives appropriately.

Pharmacological Test

Inhibitory effects on TNF-α production induced by lipopolysaccharide (LPS) stimulation were studied by in vivo tests according to the method of McGeehan et al. (Nature, 370, 558–561 (1994)).

Female rats (five per group), body weight of about 200 g, about eight weeks old, were used as test animals. LPS from Salmonella was dissolved in physiological saline to prepare an LPS solution (1 mg/ml). Test compounds were dissolved or uniformly suspended in a 1% aqueous methylcellulose solution to give test compound preparation liquids.

The above-mentioned LPS solution (0.5 ml/kg) was subcutaneously administered to the rat. Immediately after the LPS administration, the test compound preparation liquid (5 ml/kg, containing 10 mg/kg test compound) was orally administered. Two hours after the LPS administration, blood was collected from abdominal aorta and was centrifuged at 4° C. and 3000 rpm for ten minutes. TNF-α levels in the obtained plasma were measured with a rat TNF-α -specific ELISA kit. TNF-α was not observed in the plasma with respect to an LPS-nonadministered group (control).

TNF-α production inhibition rates of the test compounds were determined by the following equation.

Inhibition rate (%)=[(A−B)/A]×100

A: TNF-α level in plasma of test compound-nonadministered group
B: TNF-α level in plasma of test compound-administered group (Results)

Table 1 shows TNF-α production inhibition rates (%) by oral administration of 10 mg/kg.

TABLE 1

| Test compound | Inhibition rate (%) |
|---|---|
| Compound No. 4-2 | 72.5 |
| Compound No. 4-3 | 80.8 |
| Compound No. 4-15 | 77.3 |
| Compound No. 4-16 | 77.2 |
| Compound No. 4-17 | 70.6 |
| Compound No. 4-18 | 64.2 |
| Compound No. 5-1 | 74.9 |
| Compound No. 5-2 | 81.2 |
| Compound No. 8-1 | 80.0 |
| Compound No. 8-3 | 78.9 |
| Compound No. 8-4 | 81.0 |
| Compound No. 8-10 | 69.0 |
| Compound No. 8-11 | 63.6 |

From the above-mentioned results, it is apparent that the present compounds exhibit excellent TNF-α production inhibitory effects and have various medical uses as therapeutic agents for diseases in which TNF-α participates, for example, autoimmune diseases such as rheumatoid arthritis, Crohn's disease and systemic lupus erythematosus, cachexia, acute infectious disease, allergy, pyrexia, anemia, diabetes and the like.

INDUSTRIAL APPLICABILITY

The present invention provides novel urea derivatives which have TNF-α production inhibitory effects and are useful as therapeutic agents for various diseases, particularly as therapeutic agents for autoimmune diseases such as rheumatoid arthritis.

What is claimed is:

1. A compound represented by the following formula [I] or a salt thereof, $$R^1-S-\underset{R^2}{\underset{|}{A^1}}-\underset{R^3}{\underset{|}{N}}-\underset{O}{\overset{||}{C}}-\underset{R^4}{\underset{|}{N}}-\underset{R^5}{\underset{|}{A^2}}-R^6 \quad [I]$$

wherein $R^1$ is hydrogen, lower alkyl, phenyl or a group of the following formula [II].

$$-S-\underset{R^2}{\underset{|}{A^1}}-\underset{R^3}{\underset{|}{N}}-\underset{O}{\overset{||}{C}}-\underset{R^4}{\underset{|}{N}}-\underset{R^5}{\underset{|}{A^2}}-R^6 \quad [II]$$

$R^2$ is hydrogen, lower alkyl, cycloalkyl, phenyl, carboxyl or ester thereof, and can join with sulfur adjacent to $A^1$ to form a nonaromatic heterocycle having sulfur in the ring;

$R^3$ and $R^4$, being the same or different, are hydrogen, lower alkyl, lower alkenyl, cycloalkyl, cycloalkenyl or phenyl;

$R^5$ is hydrogen, lower alkyl, hydroxy or lower alkoxy;

$R^6$ is an aromatic heterocycle having nitrogen in the ring;

$A^1$ and $A^2$, being the same or different, are lower alkylene;

provided that when $R^6$ is imidazolyl or purinyl, at least one of $R^3$ and $R^4$ is not hydrogen;

each lower alkyl defined above can be substituted by cycloalkyl, cycloalkenyl, adamantyl, phenyl, halogen, hydroxy, lower alkoxy or an aromatic or nonaromatic heterocycle having nitrogen in the ring;

each phenyl defined above can be substituted by lower alkyl, phenyl, hydroxy, lower alkoxy, halogeno-lower alkoxy, halogen, nitro, carboxyl or ester thereof; and the aromatic or nonaromatic heterocycle having nitrogen in the ring defined above can be substituted by lower alkyl, halogeno-lower alkyl, hydroxy-lower alkyl, cycloalkyl, phenyl, halogen, hydroxy or lower alkoxy; and wherein thiol, hydroxy and/or nitrogen of the non-aromatic heterocycle or the aromatic heterocycle are optionally protected with a protecting group, wherein the optional thiol protecting group is an acyl or substituted thiol;

the optional hydroxy protecting group acyl, substituted lower alkyl or substituted silyl; and the optional protecting group or the nitrogen of the non-aromatic heterocycle or the aromatic heterocycle is acyl, substituted lower alkyl or substituted sulfonyl.

2. The compound or a salt thereof as claimed in claim 1, wherein the aromatic heterocycle having nitrogen in the ring is selected from a pyridine ring, a pyrimidine ring, a pyrrole ring, an imidazole ring, an oxazole ring, a thiazole ring, a quinoline ring, an indole ring, a benzimidazole ring, a benzoxazole ring and a benzothiazole ring, the nonaromatic heterocycle having nitrogen in the ring is selected from a piperidine ring, a morpholine ring, a piperazine ring and a homopiperazine ring, and the nonaromatic heterocycle having sulfur in the ring is selected from a tetrahydrothiophene ring and a thiolactone ring.

3. The compound or a salt thereof as claimed in claim 1, wherein

1) $R^1$ is a group selected from hydrogen, lower alkyl and a group of the following formula [II], wherein the lower alkyl can be substituted by phenyl $$-S-\underset{R^2}{\underset{|}{A^1}}-\underset{R^3}{\underset{|}{N}}-\underset{O}{\overset{||}{C}}-\underset{R^4}{\underset{|}{N}}-\underset{R^5}{\underset{|}{A^2}}-R^6; \quad [II]$$

and/or

2) $R^2$ is a group selected from hydrogen, lower alkyl, carboxyl and ester thereof; and/or 3) $R^2$ is a group joining with sulfur adjacent to $A^1$ to form a nonaromatic heterocycle selected from a tetrahydrothiophene ring and a thiolactone ring; and/or 4) $R^3$ and $R^4$, being the same or different, are groups selected from hydrogen and lower alkyl, wherein the lower alkyl can be substituted by a group selected from cycloalkyl, cycloalkenyl, adamantyl, phenyl, a pyridine ring and a piperidine ring, and further the phenyl can be substituted by a group selected from halogeno-lower alkoxy, halogen, carboxyl and ester thereof; and/or 5) $R^5$ is a group selected from hydrogen and lower alkyl; and/or 6) $R^6$ is an aromatic heterocycle having nitrogen in the ring selected from a pyridine ring, a pyrimidine ring, a pyrrole ring, an imidazole ring, a thiazole ring, an indole ring, a benzimidazole ring and a benzothiazole ring, wherein the aromatic heterocycle can be substituted by lower alkyl;

provided that when $R^6$ is imidazolyl or purinyl, at least one of $R^3$ and $R^4$ is not hydrogen.

4. The compound or a salt thereof as claimed in claim 1, wherein

1) $R^1$ is a group selected from hydrogen and lower alkyl; and/or
2) $R^2$ is hydrogen; and/or
3) $R^3$ is lower alkyl, wherein the lower alkyl can be substituted by a group selected from cycloalkyl, cycloalkenyl, adamantyl and phenyl, and further the phenyl can be substituted by halogen; and/or
4) $R^4$ is hydrogen; and/or
5) $R^5$ is hydrogen; and/or
6) $R^6$ is a pyridine ring.

5. The compound or a salt thereof as claimed in claim 1, wherein

1) $R^1$ is a group selected from hydrogen, methyl, benzyl and a group of the following formula [II]

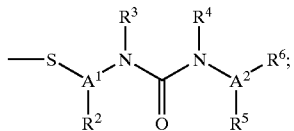

and/or

2) $R^2$ is a group selected from hydrogen, isopropyl and methoxycarbonyl; and/or
3) $R^2$ is a group joining with sulfur adjacent to $A^1$ to form a 2-oxotetrahydrothiophene ring or a tetrahydrothiophene ring; and/or
4) $R^3$ is a group selected from hydrogen, isopentyl, 2-cyclopentylethyl, 2-cyclohexylethyl, 2-cycloheptylethyl, 2-cyclooctylethyl, 2-(cyclohexen-1-yl)ethyl, 1-adamantylmethyl, 2-(1-adamantyl)ethyl, phenethyl, 2,2-diphenylethyl, 3-phenylpropyl, 4-fluorophenethyl, 4-(ethoxycarbonyl)phenethyl, 4-(trifluoro-methoxy)phenethyl, 2-(1-piperidyl)ethyl and 2-(4-pyridyl)ethyl; and/or
5) $R^4$ is a group selected from hydrogen, 2-cyclohexylethyl and phenethyl; and/or
6) $R^5$ is hydrogen or methyl; and/or
7) $R^6$ is a group selected from 1-pyrrolyl, 1-imidazolyl, 4-(1-methylimidazolyl), 4-(2-methylthiazolyl), 2-pyridyl, 3-pyridyl, 4-pyridyl, 4-(1-methylpyridinium), 4-pyrimidinyl, 3-indolyl, 2-benzimidazolyl and 2-benzothiazolyl; and/or
8) $A^1$ is ethylene or isopropylethylene; and/or
9) $A^2$ is a group selected from methylene, ethylene, methylmethylene, propylene, tetramethylene and pentamethylene;

provided that when $R^6$ is imidazolyl or purinyl, at least one of $R^3$ and $R^4$ is not hydrogen.

6. The compound or a salt thereof as claimed in claim 1, wherein

1) $R^1$ is a group selected from hydrogen and methyl; and/or
2) $R^2$ is hydrogen; and/or
3) $R^3$ is a group selected from 2-cyclopentylethyl, 2-cyclohexylethyl, 2-(cyclohexen-1-yl)ethyl, 2-(1-adamantyl)ethyl, phenethyl, 3-phenylpropyl and 4-fluorophenethyl; and/or 4) $R^4$ is hydrogen; and/or
5) $R^5$ is hydrogen; and/or
6) $R^6$ is a group selected from 3-pyridyl and 4-pyridyl; and/or
7) $A^1$ is ethylene; and/or
8) $A^2$ is a group selected from methylene, ethylene and propylene.

7. The compound or a salt thereof as claimed in claim 1, wherein thiol, hydroxy and/or nitrogen of the nonaromatic heterocycle or the aromatic heterocycle is protected with a protecting group.

8. The compound or a salt thereof as claimed in claim 2, wherein thiol, hydroxy and/or nitrogen of the nonaromatic heterocycle or the aromatic heterocycle is protected with a protecting group.

9. The compound or a salt thereof as claimed in claim 3, wherein thiol, hydroxy and/or nitrogen of the nonaromatic heterocycle or the aromatic heterocycle is protected with a protecting group.

10. The compound or a salt thereof as claimed in claim 4, wherein thiol, hydroxy and/or nitrogen of the nonaromatic heterocycle or the aromatic heterocycle is protected with a protecting group.

11. The compound or a salt thereof as claimed in claim 5, wherein thiol, hydroxy and/or nitrogen of the nonaromatic heterocycle or the aromatic heterocycle is protected with a protecting group.

12. The compound or a salt thereof as claimed in claim 6, wherein thiol, hydroxy and/or nitrogen of the nonaromatic heterocycle or the aromatic heterocycle is protected with a protecting group.

13. The compound or a salt thereof as claimed in claim 7, wherein the thiol is protected with acetyl.

14. The compound or a salt thereof as claimed in claim 8, wherein the thiol is protected with acetyl.

15. The compound or a salt thereof as claimed in claim 9, wherein the thiol is protected with acetyl.

16. The compound or a salt thereof as claimed in claim 10, wherein the thiol is protected with acetyl.

17. The compound or a salt thereof as claimed in claim 11, wherein the thiol is protected with acetyl.

18. The compound or a salt thereof as claimed in claim 12, wherein the thiol is protected with acetyl.

19. The compound or a salt thereof as claimed in claim 13, wherein the thiol is protected with acetyl.

20. A pharmaceutical composition containing a compound or a salt thereof as an active ingredient together with a carrier and wherein said compound is a compound of the following formula [I]:

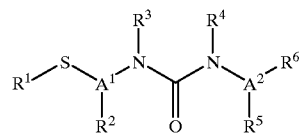

wherein $R^1$ is hydrogen, lower alkyl, phenyl or a group of the following formula [II]:

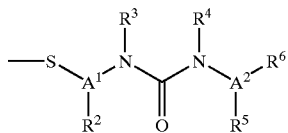

[II]

R² is hydrogen, lower alkyl, cycloalkyl, phenyl, carboxyl or ester thereof, and can join with sulfur adjacent to A¹ to form a nonaromatic heterocycle having sulfur in the ring;

R³ and R⁴, being the same or different, are hydrogen, lower alkyl, lower alkenyl, cycloalykl, cycloalkenyl, or phenyl;

R⁵ is hydrogen, lower alkyl, hydroxy or lower alkoxy;

R⁶ is an aromatic heterocycle having nitrogen in the ring;

A¹ and A², being the same or different, are lower alkylene;

each lower alkyl defined above can be substituted by cycloalkyl, cycloalkenyl, adamantyl, phenyl, halogen, hydroxy, lower alkoxy or an aromatic or nonaromatic heterocycle having nitrogen in the ring;

each phenyl defined above can be substituted by lower alkyl, phenyl, hydroxy, lower alkoxy, halgeno-lower alkoxy, halogen nitro, carboxyl or ester thereof; and the aromatic or nonaromatic heterocycle having nitrogen in the ring defined above can be substituted by lower alkyl, halogeno-lower alkyl, hydroxy-lower alkyl, cycloalkyl, phenyl halogen, hydroxy or lower alkoxy.

21. A method of treating a person having a disease susceptible to treatment by inhibition of TNF-α production comprising administering to said person an amount of a compound or a salt thereof effective to inhibit TNF-α production in said person, and wherein said compound is a compound of the following formula [I]:

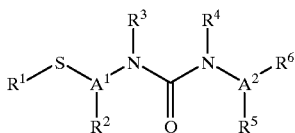

[I]

wherein R¹ is hydrogen, lower alkyl, phenyl or a group of the following formula [II]:

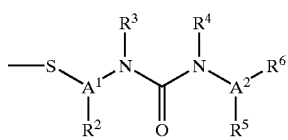

[II]

R² is hydrogen, lower alkyl, cycloalkyl, phenyl, carboxyl or ester thereof, and can join with sulfur adjacent to A¹ to form a nonaromatic heterocycle having sulfur in the ring;

R³ and R⁴, being the same or different, are hydrogen, lower alkyl, lower alkenyl, cycloalykl, cycloalkenyl, or phenyl;

R⁵ is hydrogen, lower alkyl, hydroxy or lower alkoxy;

R⁶ is an aromatic heterocycle having nitrogen in the ring;

A¹ and A², being the same or different, are lower alkylene;

each lower alkyl defined above can be substituted by cycloalkyl, cycloalkenyl, adamantyl, phenyl, halogen, hydroxy, lower alkoxy or an aromatic or nonaromatic heterocycle having nitrogen in the ring;

each phenyl defined above can be substituted by lower alkyl, phenyl, hydroxy, lower alkoxy, halgeno-lower alkoxy, halogen nitro, carboxyl or ester thereof; and the aromatic or nonaromatic heterocycle having nitrogen in the ring defined above can be substituted by lower alkyl, halogeno-lower alkyl, hydroxy-lower alkyl, cycloalkyl, phenyl halogen, hydroxy or lower alkoxy.

22. A method of treating a person suffering from an autoimmune disease comprising administering to said person an effective amount of a compound or a salt thereof wherein said compound is a compound of the following formula [I]:

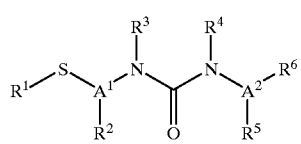

[I]

wherein R¹ is hydrogen, lower alkyl, phenyl or a group of the following formula [II]:

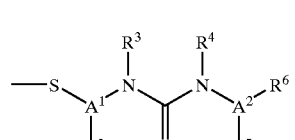

[II]

R² is hydrogen, lower alkyl, cycloalkyl, phenyl, carboxyl or ester thereof, and can join with sulfur adjacent to A¹ to form a nonaromatic heterocycle having sulfur in the ring;

R³ and R⁴, being the same or different, are hydrogen, lower alkyl, lower alkenyl, cycloalykl, cycloalkenyl, or phenyl;

R⁵ is hydrogen, lower alkyl, hydroxy or lower alkoxy;

R⁶ is an aromatic heterocycle having nitrogen in the ring;

A¹ and A², being the same or different, are lower alkylene;

each lower alkyl defined above can be substituted by cycloalkyl, cycloalkenyl, adamantyl, phenyl, halogen, hydroxy, lower alkoxy or an aromatic or nonaromatic heterocycle having nitrogen in the ring;

each phenyl defined above can be substituted by lower alkyl, phenyl, hydroxy, lower alkoxy, halgeno-lower alkoxy, halogen nitro, carboxyl or ester thereof; and the aromatic or nonaromatic heterocycle having nitrogen in the ring defined above can be substituted by lower alkyl, halogeno-lower alkyl, hydroxy-lower alkyl, cycloalkyl, phenyl halogen, hydroxy or lower alkoxy.

23. A method of treating a person suffering from a rheumatic disease comprising administering to said person an effective amount of a compound or salt thereof wherein said compound is a compound of the following formula [I]:

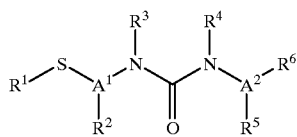

[I]

wherein $R^1$ is hydrogen, lower alkyl, phenyl or a group of the following formula [II]:

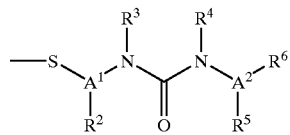

[II]

$R^2$ is hydrogen, lower alkyl, cycloalkyl, phenyl, carboxyl or ester thereof, and can join with sulfur adjacent to $A^1$ to form a nonaromatic heterocycle having sulfur in the ring;

$R^3$ and $R^4$, being the same or different, are hydrogen, lower alkyl, lower alkenyl, cycloalykl, cycloalkenyl, or phenyl;

$R^5$ is hydrogen, lower alkyl, hydroxy or lower alkoxy;

$R^6$ is an aromatic heterocycle having nitrogen in the ring;

$A^1$ and $A^2$, being the same or different, are lower alkylene;

each lower alkyl defined above can be substituted by cycloalkyl, cycloalkenyl, adamantyl, phenyl, halogen, hydroxy, lower alkoxy or an aromatic or nonaromatic heterocycle having nitrogen in the ring;

each phenyl defined above can be substituted by lower alkyl, phenyl, hydroxy, lower alkoxy, halgeno-lower alkoxy, halogen nitro, carboxyl or ester thereof; and the aromatic or nonaromatic heterocycle having nitrogen in the ring defined above can be substituted by lower alkyl, halogeno-lower alkyl, hydroxy-lower alkyl, cycloalkyl, phenyl halogen, hydroxy or lower alkoxy.

* * * * *